US011369467B2

(12) United States Patent
Chacón Quirós et al.

(10) Patent No.: US 11,369,467 B2
(45) Date of Patent: Jun. 28, 2022

(54) MEDICAL IMAGING SYSTEMS, DEVICES, AND METHODS

(71) Applicant: Establishment Labs S.A., Alajuela (CR)

(72) Inventors: Juan José Chacón Quirós, Alajuela (CR); Rafael G. Corrales, San José (CR); Gerardo Mora, Alajuela (CR); Ana Y. Quiros, Alajuela (CR); Celso P. Garcia, Alajuela (CR); Jorge Mayorga, Alajuela (CR); Mario Ramirez, Alajuela (CR); Federico Carbo, Alajuela (CR)

(73) Assignee: Establishment Labs S.A., Alajuela (CR)

( * ) Notice: Subject to any disclaimer, the term of this patent is extended or adjusted under 35 U.S.C. 154(b) by 707 days.

(21) Appl. No.: 16/091,248

(22) PCT Filed: Apr. 4, 2017

(86) PCT No.: PCT/IB2017/000380
§ 371 (c)(1),
(2) Date: Oct. 4, 2018

(87) PCT Pub. No.: WO2017/175055
PCT Pub. Date: Oct. 12, 2017

(65) Prior Publication Data
US 2019/0117379 A1 Apr. 25, 2019

Related U.S. Application Data

(60) Provisional application No. 62/334,667, filed on May 11, 2016, provisional application No. 62/318,402, filed on Apr. 5, 2016.

(51) Int. Cl.
*A61B 5/00* (2006.01)
*A61B 5/107* (2006.01)
(Continued)

(52) U.S. Cl.
CPC .............. *A61F 2/12* (2013.01); *A61B 5/0062* (2013.01); *A61B 5/0064* (2013.01);
(Continued)

(58) Field of Classification Search
CPC .... A61F 2/12; A61F 2240/004; A61B 5/0062; A61B 5/107; A61B 5/0064;
(Continued)

(56) References Cited

U.S. PATENT DOCUMENTS 5,686,992 A 11/1997 Kawamoto
2010/0026789 A1* 2/2010 Balogh .................. A61B 6/022
348/50
(Continued)

FOREIGN PATENT DOCUMENTS

CN 104243758 A 12/2014
KR 20030071102 A 9/2003
(Continued)

OTHER PUBLICATIONS

Lucini, C.B., "Lucida: The 3 D Laser Scanner For Conservation," *Lidar News Magazine*, vol. 5, No. 2, XP002771168 (2015).
(Continued)

*Primary Examiner* — Jared Walker
(74) *Attorney, Agent, or Firm* — Schwegman Lundberg & Woessner, P.A.

(57) ABSTRACT

Systems, methods, and devices useful in medical procedures, such as, e.g., aesthetic and/or reconstructive surgeries, are described. The system may be an imaging system that includes a database and a computer system configured to create, modify, and/or display three-dimensional images created from digital image data of an anatomical region of a subject. The digital image data may be obtained with an imaging device such as a scanner.

16 Claims, 21 Drawing Sheets

(51) Int. Cl.
*H04N 13/254* (2018.01)
*H04N 13/239* (2018.01)
*G06T 15/08* (2011.01)
*A61F 2/12* (2006.01)

(52) U.S. Cl.
CPC .......... *A61B 5/0077* (2013.01); *A61B 5/0091* (2013.01); *A61B 5/107* (2013.01); *A61B 5/1077* (2013.01); *A61B 5/1079* (2013.01); *G06T 15/08* (2013.01); *H04N 13/239* (2018.05); *H04N 13/254* (2018.05); *A61B 2576/02* (2013.01); *A61F 2240/004* (2013.01); *G06T 2200/08* (2013.01); *G06T 2215/16* (2013.01)

(58) Field of Classification Search
CPC ... A61B 5/0077; A61B 5/0091; A61B 5/1077; A61B 5/1079; A61B 2576/02; H04N 13/254; H04N 13/239; G06T 15/08; G06T 2200/08; G06T 2215/16
See application file for complete search history.

(56) References Cited

U.S. PATENT DOCUMENTS

| | | | |
|---|---|---|---|
| 2011/0243409 A1* | 10/2011 | Naimi | A61B 5/0091 382/128 |
| 2014/0218720 A1* | 8/2014 | Kindem | A61B 5/0035 356/72 |
| 2015/0257651 A1* | 9/2015 | Angott | A61B 5/4312 600/474 |
| 2015/0304530 A1* | 10/2015 | Courteille | H04N 13/243 348/48 |

FOREIGN PATENT DOCUMENTS

| | | |
|---|---|---|
| TW | M 515096 U | 1/2016 |
| WO | WO 2010/047523 A2 | 4/2010 |
| WO | WO 2011/158143 A1 | 12/2011 |

OTHER PUBLICATIONS

International Search Report for PCT/IB2017/000380 dated Sep. 18, 2017 (5 pages).

* cited by examiner

MEDICAL IMAGING SYSTEMS, DEVICES, AND METHODS

CROSS-REFERENCE TO RELATED APPLICATIONS

This application is a U.S. national stage filing under 35 U.S.C. § 371 of International Application No. PCT/IB2017/000380, filed on Apr. 4, 2017, which claims the benefits of priority from U.S. Provisional Application No. 62/318,402, filed on Apr. 5, 2016, and U.S. Provisional Application No. 62/334,667, filed on May 11, 2016, each of which is incorporated by reference herein in its entirety.

TECHNICAL FIELD

The current disclosure relates to systems, methods, and devices useful for medical procedures, such as, e.g., aesthetic and/or reconstructive surgeries.

BACKGROUND

Aesthetic, cosmetic, and reconstructive surgeries (collectively referred to as plastic surgery) refer to surgeries performed in order to repair, restore, or change the appearance of a subject's body part. For example, cosmetic surgery includes surgeries such as rhinoplasty (remodeling the nose), rhytidectomy (facelifts), and mammoplasty (changing the size of the breasts), and reconstructive surgery includes such procedures as the reattachment of an amputated finger or toe, or implanting a prosthesis. In some such procedures, a plastic surgeon inserts a suitable implant at a desired region of the subject's body. In some cases, the subject may have to wait for the conclusion of the procedure to visualize the results of the procedure. Embodiments of the current disclosure may alleviate the problems discussed above and/or other problems in the art. The scope of the current disclosure, however, is defined by the attached claims, and not by the ability to solve any specific problem.

SUMMARY

Embodiments of the present disclosure relate to systems, methods, and devices useful for medical procedures, including, e.g., plastic surgery. Various aspects of the present disclosure may be useful for planning, simulating, and/or evaluating the outcome of cosmetic surgery, reconstructive surgery, and/or other medical procedures.

In some embodiments, a scanner is disclosed. The scanner may include a cart coupled to a rail. The cart may be configured to move along the rail in a first direction, and the rail may be configured to move with the cart in a second direction different from the first direction. The scanner may also include an imaging device coupled to the cart. The imaging device may be configured to capture a three-dimensional image of a subject. The subject may be a client or patient contemplating a medical procedure, for example.

Additionally or alternatively, embodiments of the scanner may include one or more of the following features: the second direction may be transverse to the first direction; the imaging device may be configured to rotate about at least one of a first axis extending in the first direction, or a second axis extending in the second direction; the scanner may further include one or more light sources; the one or more light sources may include one or more white light lights and one or more yellow lights; the scanner may include a first motor configured to move the cart along the rail in the first direction, and a second motor configured to move the rail along with the cart in the second direction; the scanner may further include one or more sensors configured to detect a position of the cart on the rail; the rail may be curved in an arc; the imaging device may include multiple cameras; and/or one or more cameras of the multiple cameras may include different focal points. For example, the scanner may include a first camera having a first focal point and a second camera having a second focal point different than the first focal point. In some examples of the current disclosure, the cart and/or the imaging device may include a housing, wherein the camera(s) are removably attached to the housing. In other aspects of the current disclosure, the camera(s) are not removable from the housing of the cart and/or imaging device. Further, for example, the first direction may be substantially perpendicular to the second direction.

In some embodiments, a method of operating a scanner including one or more cameras configured to capture a three-dimensional image of a subject is disclosed. The method may include activating the one or more cameras. The one or more cameras may be coupled to a cart movably coupled to a rail. The method may also include moving the cart along the rail in a first direction, and moving the rail with the cart in a second direction different from the first direction. In at least some embodiments of the current disclosure, the first direction may be transverse, e.g., substantially perpendicular, to the second direction.

Additionally or alternatively, embodiments of the method may include one or more of the following aspects: activating one or more light sources of the scanner; the one or more light sources may include one or more white lights and one or more yellow lights, and wherein activating the one or more light sources may include selectively activating the one or more white lights and the one or more yellow lights based on a skin tone of the subject; activating the one or more light sources may further include adjusting an intensity of the one or more white lights and the one or more yellow lights; moving the cart along the rail may include moving the cart in a curved path; the rail may extend from a first end to a second end, and wherein moving the cart along the rail may include moving the cart to the first end, and moving the cart from the first end to the second end; moving the cart to the first end may include rotating the one or more cameras by an angle between about 5-30 degrees about an axis extending in the second direction as the cart moves towards the first end, and moving the cart from the first end to the second end may include rotating the one or more cameras by an angle between about negative 5-30 degrees about the axis as the cart moves towards the second end; moving the rail with the cart may include moving the rail in the second direction transverse to the first direction after moving the cart to the first end, and before moving the cart from the first end to the second end; moving the cart and moving the rail with the cart may together move the one or more cameras along a substantially rectangular path.

In some embodiments, an imaging system is disclosed. The imaging system may include a scanner configured to scan an anatomical region of a subject. The scanner may include one or more cameras configured to produce image data of the anatomical region. The scanner may also include a first motor configured to move the one or more cameras along a rail in a first direction, and a second motor configured to move the rail with the one or more cameras in a second direction transverse to the first direction. The imaging system may also include a computer system operatively coupled to the scanner. The computer system may be configured to control the first motor and the second motor, receive the image data from the scanner, and construct a three-dimensional image of the anatomical region based on the image data.

Additionally or alternatively, embodiments of the method may include one or more of the following aspects: the computer system may be further configured to convert the constructed three-dimensional image of the anatomical region to a modified three-dimensional image, the modified three-dimensional image may be indicative of an expected outcome of a medical procedure on the anatomical region; the computer system may include a display device to present the constructed three-dimensional image and the modified three-dimensional image; the modified three-dimensional image may represent the expected outcome of an implantation procedure on the anatomical region; the computer system may include a database listing multiple implants, and wherein the modified three-dimensional image may be an expected outcome of embedding an implant selected from the multiple implants in the anatomical region; the modified three-dimensional image may represent the expected outcome of a reconstruction surgery on the anatomical region; the modified three-dimensional image may represent the expected outcome of an implant removal surgery on the anatomical region; the computer system may be configured to receive input from a user and control the first motor and the second motor based on the input; the computer system may be configured to control the first motor and the second motor to move the one or more cameras in a substantially rectangular path; the scanner may include one or more white lights and one or more yellow lights, and the computer system may be further configured to selectively activate the one or more white lights and one or more yellow lights based on a skin tone of the subject; the computer system may be configured to increase a number of yellow lights activated as compared to the number of white lights activated for a darker skin tone, and increase a number of white lights activated as compared to the number of yellow lights activated for a lighter skin tone; the computer system may be further configured to rotate the one or more cameras about at least one of a first axis extending in the first direction or a second axis extending in the second direction; the computer system may be configured to rotate the one or more cameras about the second axis while the one or more cameras are moving in the first direction.

In some embodiments, a method of operating an imaging system is disclosed. The imaging system may include a scanner and a computer system configured to produce a three-dimensional image of an anatomical region of a subject. The method may include activating one or more cameras of the scanner using the computer system, and controlling the scanner using the computer system to acquire image data of the anatomical region. The controlling may include moving the one or more cameras in a first direction, and moving the one or more cameras in a second direction transverse to the first direction. The method may also include receiving image data from the scanner at the computer system, and constructing the three-dimensional image of the anatomical region based on the received image data.

Additionally or alternatively, embodiments of the method may include one or more of the following aspects: converting the constructed three-dimensional image of the anatomical region to a modified three-dimensional image, the modified three-dimensional image may be indicative of an expected outcome of a medical procedure on the anatomical region; presenting the constructed three-dimensional image and the modified three-dimensional image on a display device of the computer system; the modified three-dimensional image may represent the expected outcome of embedding an implant in the anatomical regions, or) removing an implant from the anatomical region; selecting the implant from multiple implants provided in a database of the computer system; controlling the scanner may include moving the one or more cameras in a substantially rectangular path to acquire the image data; moving the one or more cameras in a first direction may include moving the one or more cameras in the first direction from an original location to a first end of the scanner; moving the one or more cameras in a second direction may include moving the one or more cameras in the second direction for a first time period while the one or more cameras are at the first end; moving the one or more cameras in a direction opposite the first direction to a second end of the scanner opposite the first end; moving the one or more cameras in direction opposite the second direction for the first time period while the one or more cameras are at the second end;

Additionally or alternatively, embodiments of the method may include one or more of the following aspects: moving the one or more cameras in the first direction to the original location; rotating the one or more cameras about a first axis by an angle between about 5-30 degrees when the one or more cameras are moving from the original location to the first end; rotating the one or more cameras by about negative 5-30 degrees about the first axis when the one or more cameras are moving from the original location to the second end, wherein the first axis is an axis extending along the second direction; the scanner may include one or more white lights and one or more yellow lights, and controlling the scanner may include selectively activating the one or more white lights and the one or more yellow lights based on a skin tone of the subject; selectively activating may include increasing a number of yellow lights activated as compared to the number of white lights activated for a darker skin tone, and increasing a number of white lights activated as compared to the number of yellow lights activated for a lighter skin tone; receiving the image data may include receiving multiple files comprising the image data, and constructing the three-dimensional image may include compiling the received multiple files into a single file.

In some embodiments, a method of simulating a change in appearance of an anatomical region of a subject using a computer system is disclosed. The method may include obtaining a digital three-dimensional image of a torso of the subject and designing a custom breast implant based on at least one or more of the parameters of size, shape, and surface texture. The method may also include converting, using the computer system, the digital three-dimensional image to a modified three-dimensional image to simulate a change in appearance of the subject following implantation of the custom breast implant in the torso, and displaying the modified three-dimensional image indicating an expected outcome of the implantation.

Additionally or alternatively, embodiments of the method may include one or more of the following aspects: wherein obtaining the digital three-dimensional image may include controlling a scanner using the computer system to acquire image data of the torso, and processing the acquired image data to construct the digital three-dimensional image; controlling the scanner may include controlling a camera associated with the scanner to traverse a defined trajectory while acquiring the image data, and controlling illumination of the torso while acquiring the image data; creating a computer-readable model of the custom breast implant for manufacturing the custom breast implant.

In some embodiments, an imaging system for a medical procedure is disclosed. The imaging system may include a scanner configured to scan an anatomical region of a subject and produce digital image data of the anatomical region. The scanner may include a rail, a cart configured to move on the rail, and one or more cameras coupled to the cart. In some aspects of the current disclosure, the one or more cameras of the scanner include a first camera having a first focal point and a second camera having a second focal point different than the first focal point. Additionally or alternatively, the one or more cameras are removably attached to a housing of the cart. The imaging system may also include a computer system operatively coupled to the scanner. The computer system may be configured to control movement of the cart in a substantially rectangular path as the one or more cameras acquire the image data, receive the image data from the scanner, and construct a three-dimensional image of the anatomical region based on the image received data. The computer system may also be configured to convert the constructed three-dimensional image into a modified three-dimensional image based on user input, and display the modified three-dimensional image of the anatomical region indicating an expected outcome of the medical procedure based on the simulation.

Additionally or alternatively, embodiments of the imaging system may include one or more of the following aspects: the scanner may include one or more lighting sources, the computer system may be configured to control illumination of the anatomical region using the one or more lighting sources as the one or more cameras acquire the image data; the one or more lighting sources includes multiple white lights and multiple yellow lights, wherein the computer system may be configured to adjust a ratio of a number of white lights illuminated to a number of yellow lights illuminated based on at least a skin tone of the subject.

BRIEF DESCRIPTION OF THE DRAWINGS

The accompanying drawings, which are incorporated in and constitute a part of this specification, illustrate exemplary embodiments of the present disclosure. In these drawings, where appropriate, reference numerals illustrating similar elements are labeled similarly. For simplicity and clarity of illustration, the figures depict the general structure and/or manner of construction of the various embodiments. Descriptions and details of well-known features and techniques may be omitted to avoid obscuring other features. Elements in the figures are not necessarily drawn to scale. The dimensions of some features may be exaggerated relative to other features to improve understanding of the exemplary embodiments. For example, one of ordinary skill in the art appreciates that the cross-sectional views are not drawn to scale and should not be viewed as representing proportional relationships between different layers. Further, even if it is not specifically mentioned in the text, aspects described with reference to one embodiment may also be applicable to, and may be used with, other embodiments.

DETAILED DESCRIPTION

In the discussion that follows, relative terms such as "about," "substantially," "approximately," etc. are used to indicate a possible variation of +10% in a stated numeric value. It should be noted that the description set forth herein is merely illustrative in nature and is not intended to limit the embodiments of the subject matter, or the application and uses of such embodiments. Any implementation described herein as exemplary is not to be construed as preferred or advantageous over other implementations. Rather, the term "exemplary" is used in the sense of example or illustrative. The terms "comprise," "include," "have," "with," and any variations thereof are used synonymously to denote or describe non-exclusive inclusion. As such, a process, method, system, or device that uses such terms does not include only those steps, structure or elements but may include other steps, structures or elements not expressly listed or inherent to such process, method, system, or device. Further, terms such as "first," "second," and the like, if used herein, do not denote any order, quantity, or importance, but rather are used to distinguish one element from another. Similarly, terms of relative orientation, such as "front side,"

"top side," "back side," "bottom side," etc., are referenced relative to the described figures.

Figure 1:
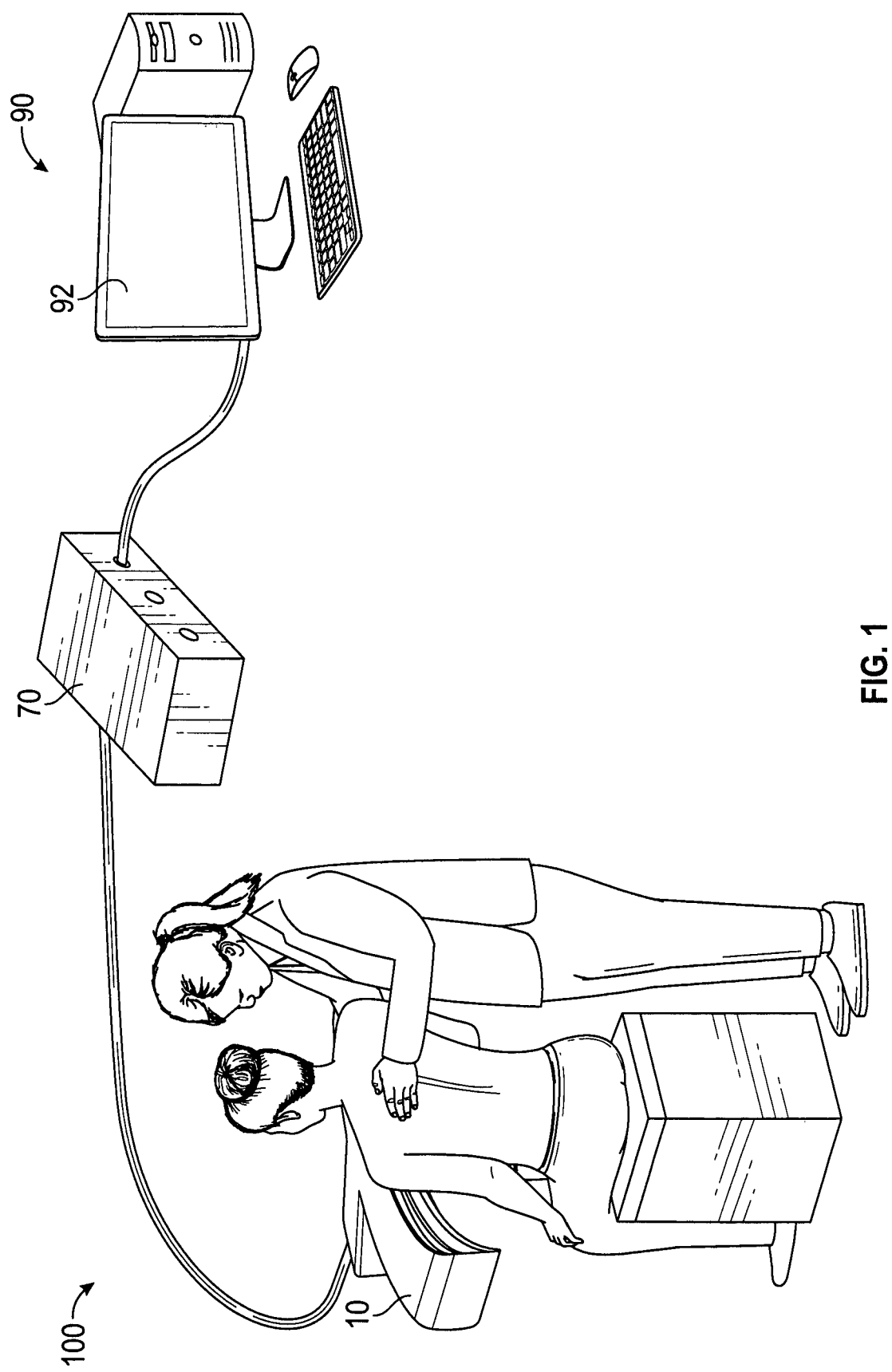
FIG. 1 illustrates an exemplary imaging system of the current disclosure.

In some embodiments, the current disclosure may include an imaging system that may be used in plastic surgery (or another medical procedure). The imaging system may be used to visualize and/or simulate expected changes in the subject's appearance resulting from plastic surgery. FIG. 1 illustrates an exemplary imaging system 100 of the current disclosure. The imaging system 100 includes an imaging scanner 10 (hereinafter scanner 10) configured to obtain one or more digital images of a subject (for e.g., a human patient considering various medical procedures) positioned in front of the scanner 10. The scanner 10 may be coupled to a controller 70 configured to manipulate and control the operations of the scanner 10. The imaging system 100 may also include a computer system 90, operatively coupled to the controller 70 and the scanner 10. The computer system 90 may be configured to direct the operations of the controller 70 and the scanner 10, and receive image data from the scanner 10. The computer system 90 may assist in creating a 3D digital image or model of the subject (akin to a digital body cast) using the data received from the scanner 10. In some embodiments, both the computer system 90 and the controller 70 may both part of, or embedded in (i.e., physically one component), the scanner 10. In some such embodiments, the display device and a user input device (keyboard, mouse, etc.) may be coupled to the integrated scanner 10, for example, using cables.

In the discussion that follows, the computer system 90 and the controller 70 are described as separate components. However, this is only exemplary. In some embodiments, both the computer system 90 and the controller 70 may be one component. For example, the features and functions of the controller 70 may be incorporated into the computer system 90, or the features and functions of the computer system 90 may be incorporated into the controller 70.

Figure 2A:
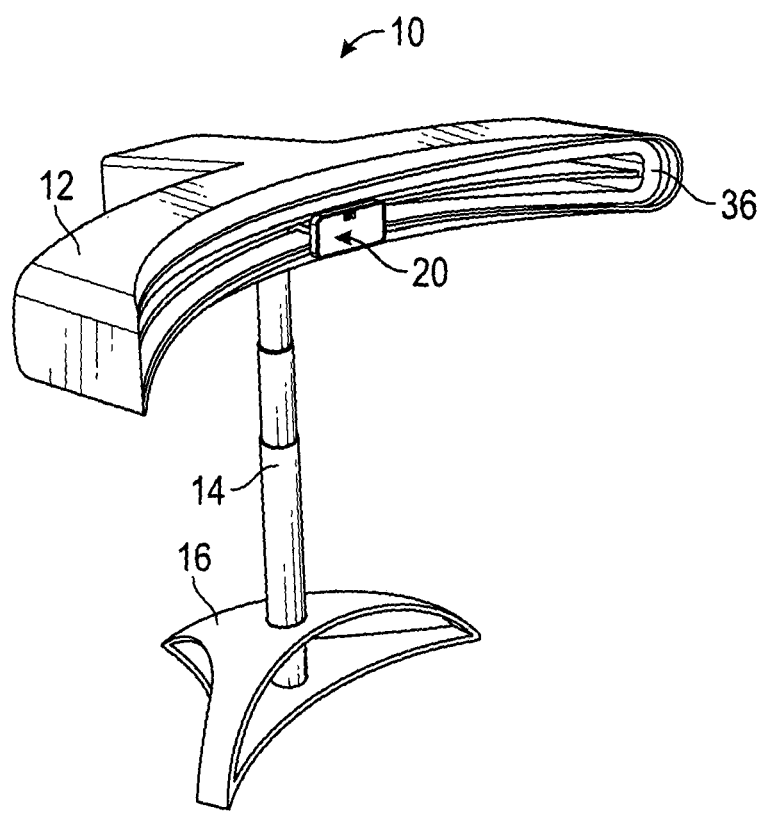
FIGS. 2A-2C illustrate different perspective views of an exemplary scanner of the imaging system of FIG. 1.
Figure 2B:
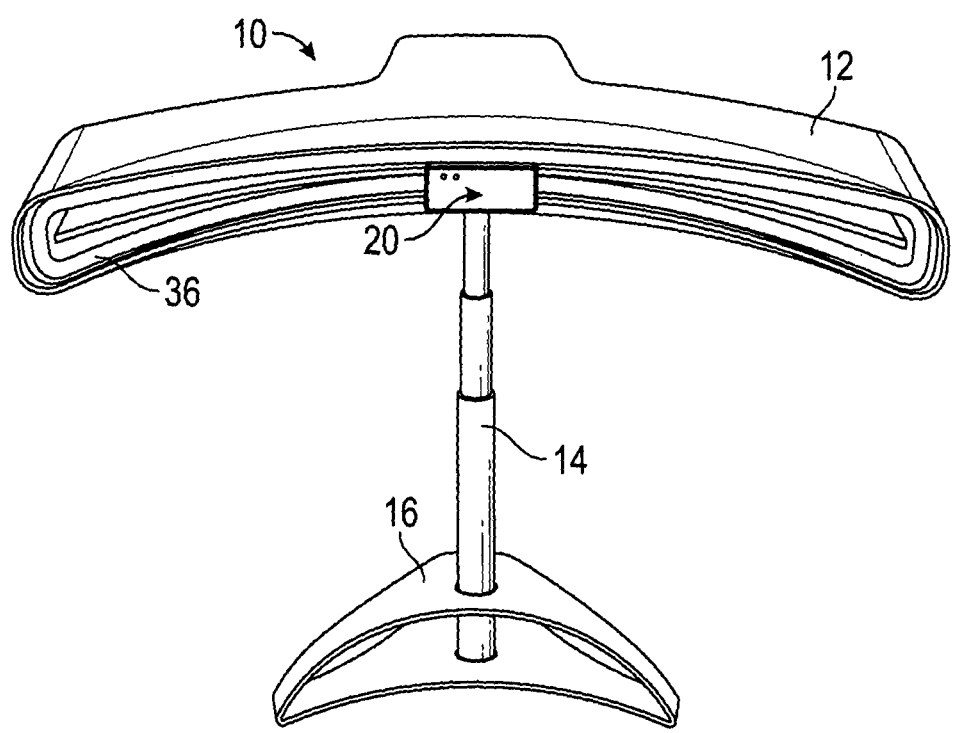
Figure 2C:
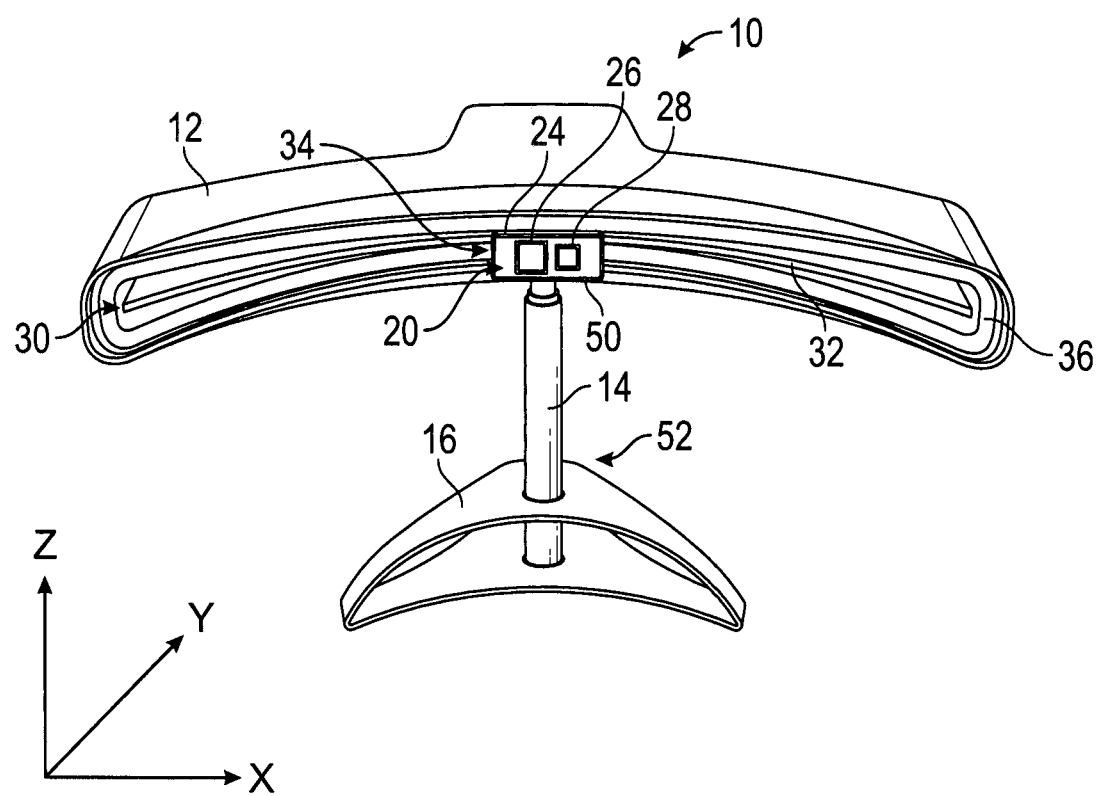
Figure 3A:
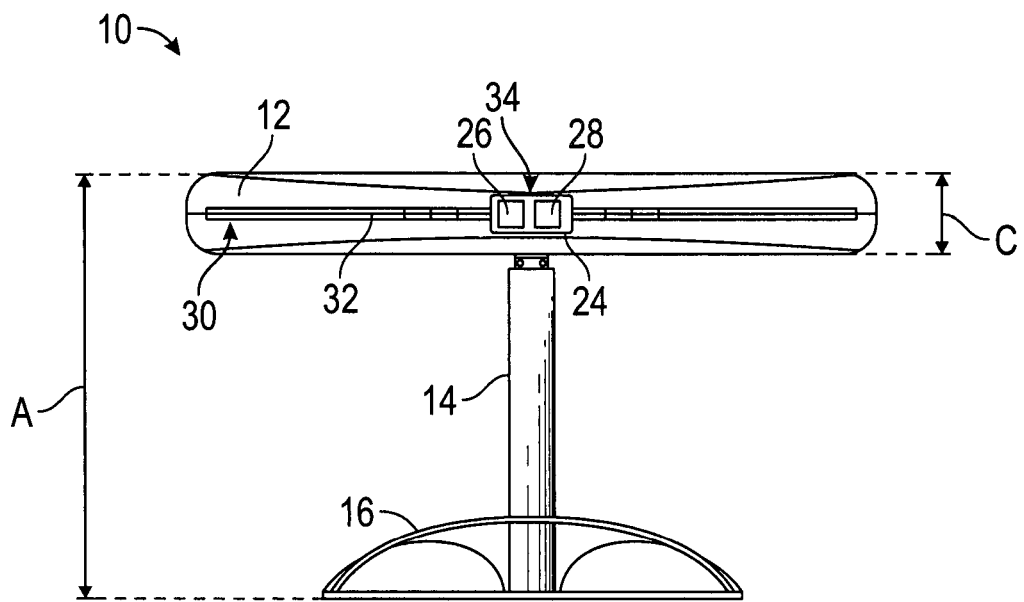
FIG. 3A illustrates a front view of an exemplary scanner of the imaging system of FIG. 1.
Figure 3B:
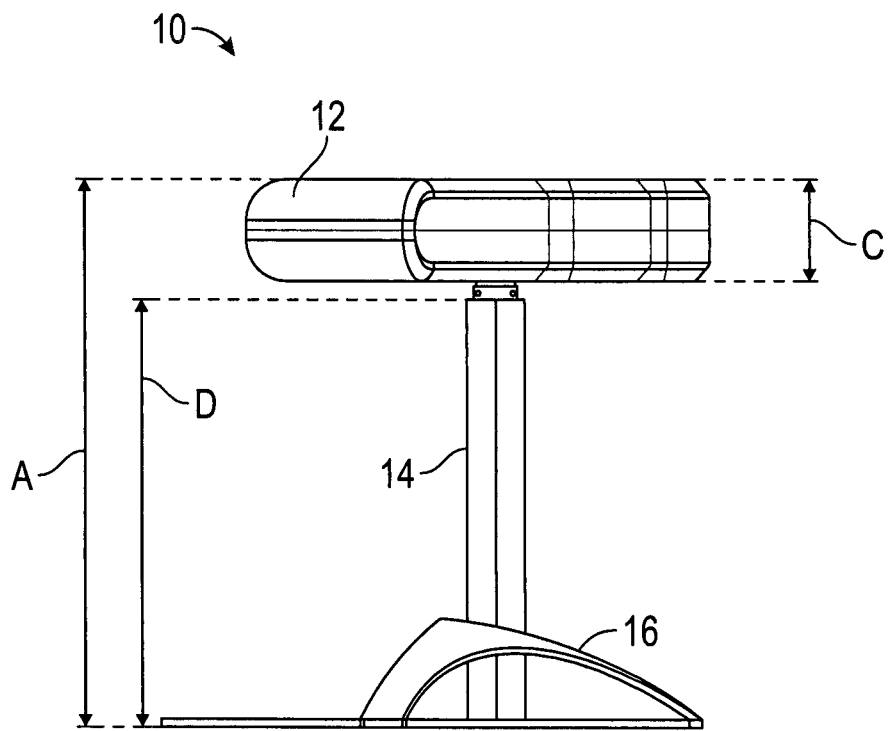
FIG. 3B illustrates a side view of an exemplary scanner of the imaging system of FIG. 1.
Figure 3C:
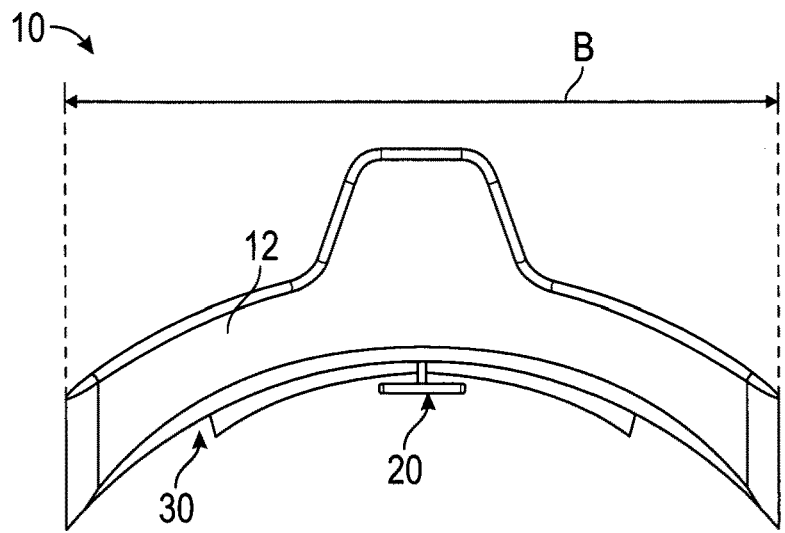
FIG. 3C illustrates a top view of an exemplary scanner of the imaging system of FIG. 1.

FIGS. 2A-2C and 3A-3C illustrate different views of an exemplary scanner 10 of the current disclosure. FIGS. 2A and 2B illustrate two perspective views of the scanner 10, and FIG. 2C is an enlarged perspective front view showing some of the features of the scanner 10. FIGS. 3A, 3B, and 3C are schematic front, side, and top views of the scanner 10. In the discussion that follows, reference will be made to FIGS. 2A-3C. Scanner 10 includes a housing 12 connected to a base 16 by a support member 14. Typically, the shape and size of housing 12 may depend upon the application. Although not a limitation, in some embodiments, the housing 12 may have a width B (see FIG. 3C) between about 100-200 cm, and a height C (see FIG. 3A) between about 1-30 cm. For some applications, housing 12 may have a width B between about 130-150 cm and a height C between about 14-25 cm. In one exemplary embodiment of scanner 10, width B is about 140.6 cm and height C is about 17.2 cm.

The base 16 of scanner 10 may have any suitable shape and dimensions for supporting the housing 12. In some embodiments, as illustrated in FIGS. 2A-3B, the base 16 may include a flat bottom, a curved upper portion, and open space between the bottom and the upper portion and have a generally triangular shape. However, this shape is only exemplary and other configurations and shapes of the base 16 are also contemplated and encompassed herein. The support member 14 of scanner 10 may extend from the bottom of the base 16, through the upper portion, to the housing 12. The length of the support member 14 may be selected such that the scanner 10 has a height and perspective suitable for collecting images of different anatomic features (e.g., torso, face, etc.) of the subject while the subject is positioned in front of the scanner (e.g., standing or seated facing the scanner). In some aspects, the support member 14 may be adjustable in length to accommodate subjects of varying size and stature. For example, the support member 14 may allow for raising and lowering (automatically or manually) the housing 12 relative to the base 16. In some embodiments, support member 14 may have a telescoping structure, and may be configured to vary in length D (see FIG. 3B) between about 70-200 cm to vary the height A (see FIG. 3B) of the scanner 10 between about 80-200 cm. In some embodiments, the scanner 10 may be configured to vary in height A between about 70-200 cm. In some embodiments, the support member 14 is not adjustable, and the scanner may have a fixed height A.

In general, the materials used in scanner 10 may have physical and chemical properties suitable for a healthcare environment (e.g., antibacterial, fire-resistant, impact-resistant, etc.). Exemplary materials suitable for the housing 12, the support member 14, and the base 16 of the scanner 10 may include polymers, metals and metal alloys, minerals (e.g., natural rock/stone materials), and combinations thereof. In some embodiments, the materials may be at least partially translucent or transparent, such that lighting components (e.g., LEDs, etc.) provided inside portions of the scanner 10 may cause light to shine through the materials. In some embodiments, the housing 12 may comprise Corian® (DuPont) or Krion® (SYSTEMPOOL, PORCELANOSA Group), a material that is a combination of aluminum trihydride and a low percentage of high-resistance resins. The scanner 10 may be a single, non-modular unit or may include separable components joined or coupled together.

As illustrated in FIGS. 2A-2C and 3C, housing 12 may have a generally curved shape in the xy plane (see triad in FIG. 2C, i.e., on a plane parallel to the floor or other surface that the base 16 is resting on. The housing 12 may include an imaging device 20 and a rail system 30 that slidably supports the imaging device 20 thereon. To obtain an image using the scanner 10, the subject may be positioned in front of the scanner 10 (e.g., at or near a focal point of the curved housing 12). The imaging device 20 of the scanner 10 may then be activated to image any portion of the body (nose, torso, etc.) of the subject. The imaging device 20 may move on the rail system 30 relative to the subject during imaging. Rail system 30 may include a rail 32 that, in some embodiments, may follow the curvature of the housing 12. A movable cart 34 may be coupled to the rail 32. The imaging device 20 may include a camera housing 24 coupled to the cart 34. The camera housing 24 may include one or more cameras 26, 28 coupled thereto. Sliding the cart 34 along the length of the rail 32 allows the cameras 26, 28 to move in arc around the subject and capture images of the subject from multiple viewpoints or angles.

The scanner 10 may also include one or more light sources (such as, for e.g., light emitting diode (LEDs) 36) to provide appropriate lighting conditions for capturing an image using the imaging device 20. Although the light sources are referred to as LEDs, other sources of light may be used. In general, any type of light emitting device (such as, bulbs, etc.) may be used in place of, or in addition to, LEDs 36. The LEDs 36 may be forward-facing (e.g., mounted on a surface generally facing the subject) on the housing 12, and arranged such that the light emitted by the LEDs 36 is generally directed toward the subject during imaging. In general, the LEDs 36 may be positioned at any suitable location on the scanner 10. In some embodiments, an array of LEDs 36 may be positioned around the rail 32 and arranged substantially along, or proximate to, the perimeter of the housing 12 (e.g., the side of the housing 12 facing the subject during imaging). In some embodiments, the scanner 10 may include groups of LEDs 36 positioned above, below, and/or on sides of the rail 32. In some embodiments, the LEDs 36 may be arranged on a strip (e.g., an adhesive strip) attached to the housing 12. In general, any number of LEDs 36 may be provided on scanner 10. Although not a requirement, in some embodiments, the total number of LEDs 36 in scanner 10 may be between about 10-5000 LEDs. For example, in some embodiments, the total number of LEDs 36 in the scanner 10 may be between 2500-3500, or 1000-3000, or 2000-5000, or 500-2000, or 10-1000, or 10-500, or 20-250, or 50-100.

The LEDs 36 may be activated (e.g., turned on and off) and controlled (e.g., change in intensity, color, etc.) by the controller 70 based on instructions from the computer system 90. In some embodiments, the computer system 90 may activate and/or control all the LEDs 36 at the same time, while in other embodiments, some of the LEDs 36 may be selectively activated and/or controlled (with respect to other LEDs 36) by the computer system 90. Some or all of the LEDs 36 may be configured to vary in intensity and generate various wavelengths of visible light (e.g., red, orange, yellow, green, blue, violet, and/or white light), infrared light, and/or ultraviolet light. In some embodiments, some LEDs 36 may be configured to generate one wavelength (e.g., color of visible light) while other LEDs 36 may be configured to generate a different wavelength. In some embodiments, some or all of the LEDs 36 may be configured to generate a range of wavelengths of light. In some embodiments, the LEDs 36 may be configured to alternate or cycle between different wavelengths, such as, for e.g., from white to blue, or from yellow to orange.

In some embodiments, the scanner 10 may include different color LEDs 36. For example, the LEDs 36 may include a plurality of white LEDs and a plurality of yellow LEDs. For example, about 30-70% of the total number of LEDs 36 may be yellow LEDs and the remaining LEDs may be white LEDs. In at least one example, the scanner 10 may include equal numbers of yellow LEDs and white LEDs. Illumination provided by the white LEDs may be referred to as cool lighting, and the illumination provided by the yellow LEDs may be referred to as warm lighting. In some embodiments, different combinations of the white and yellow LEDs may be used to provide a range of illumination suitable for subjects with different skin tones. For example, warm lighting (i.e., yellow LEDs are tuned on and white LEDs are turned off) may be used with subject's having a very fair (pale or white) skin tone, and cool lighting (i.e., white LEDs are tuned on and yellow LEDs are turned off) may be used for subjects with a very dark skin tone. Different combinations of white and yellow LEDs may be used to illuminate subjects with skin tones in between (i.e., dark and fair). Using different combinations of white and yellow LEDs 36 may provide for combinations of cool and warm colors that complement various skin types and skin tones and allow for better image quality. Illumination using combinations of white and yellow (or other color) LEDs may provide better illumination of the subject during an imaging scan and thus improve the quality of the scanned image.

As explained previously, the housing 12 and the rail 32 of scanner 10 may be curved to form arc around the subject positioned in front of the scanner 10 (see FIG. 1). In general, the housing 12 and the rail 32 may have any radius of curvature (same or different values). In some embodiments, the curvature of the housing 12 and/or the rail 32 may be at least partially based on the physical measurements of an average subject (e.g., standard measures of the adult human torso, etc.). In some embodiments, the rail 32 may have an elliptical curvature, such that the cart 34 that slides along the rail 32 may traverse an elliptical path around the subject. However, this is only exemplary. In general, the rail 32 (and housing 12) may have any curved shape and arc length such that the cart 34 traverses an arc having any desired angle and arc length around the subject. The length and curvature of the rail 32 may allow the cameras 26, 28 of the imaging device 20 to generate a range of views, from relatively narrow (e.g., an arc of about 10° around the subject) to expansive (e.g., an arc of about 270° around the subject). In some embodiments, the length and curvature of the rail 32 may be such that the cart 34 may traverse an arc of between about 10°-180° (or about 30°-90°) around a subject positioned in front of the scanner 10. It is also contemplated that, in some examples, the rail 32 forms a complete circle around the subject such that the scanner 10 generates a 360° image of the subject.

Figure 4A:
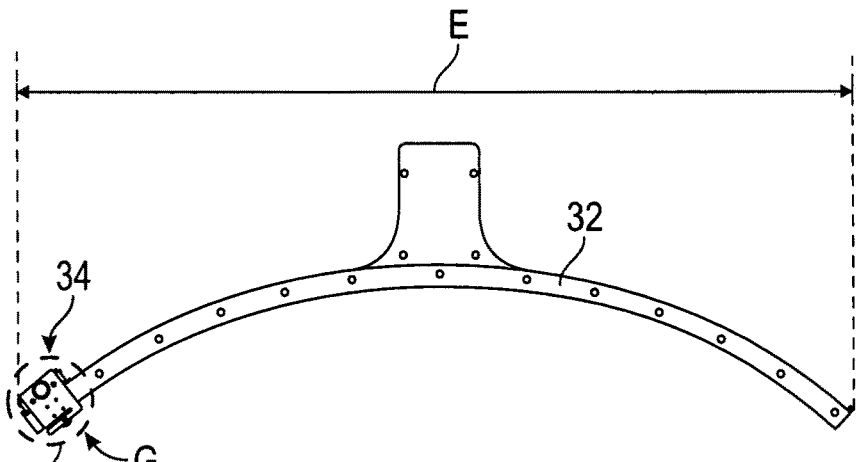
FIGS. 4A-4D illustrate different views of an exemplary rail system of the imaging system of FIG. 1.
Figure 4B:
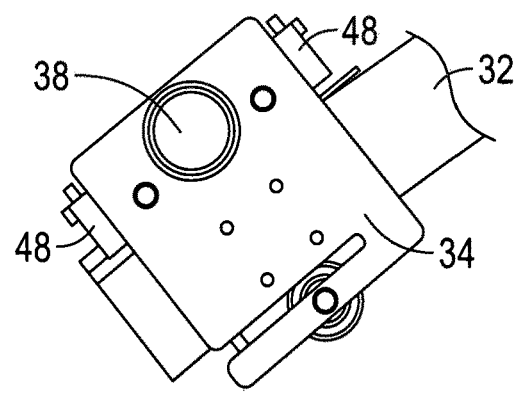
Figure 4C:
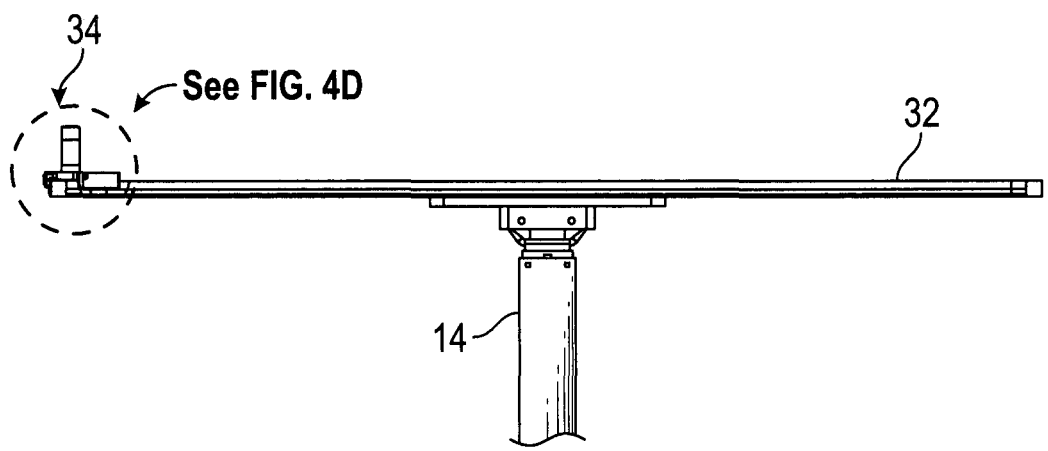
Figure 4D:
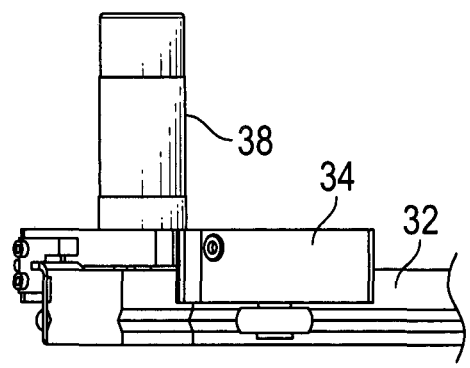
Figure 5A:
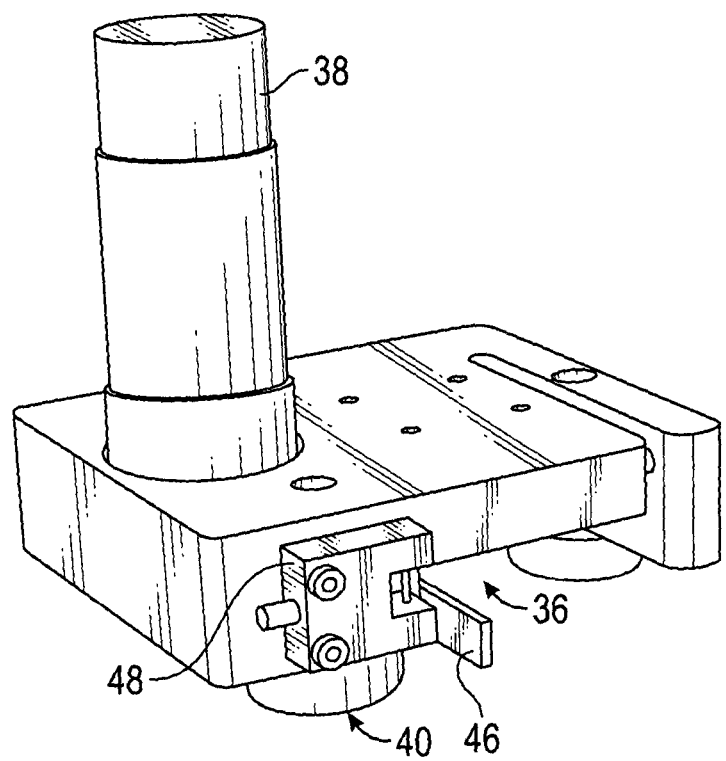
FIGS. 5A-5B illustrate different perspective views of an exemplary cart of the imaging system of FIG. 1.
Figure 5B:
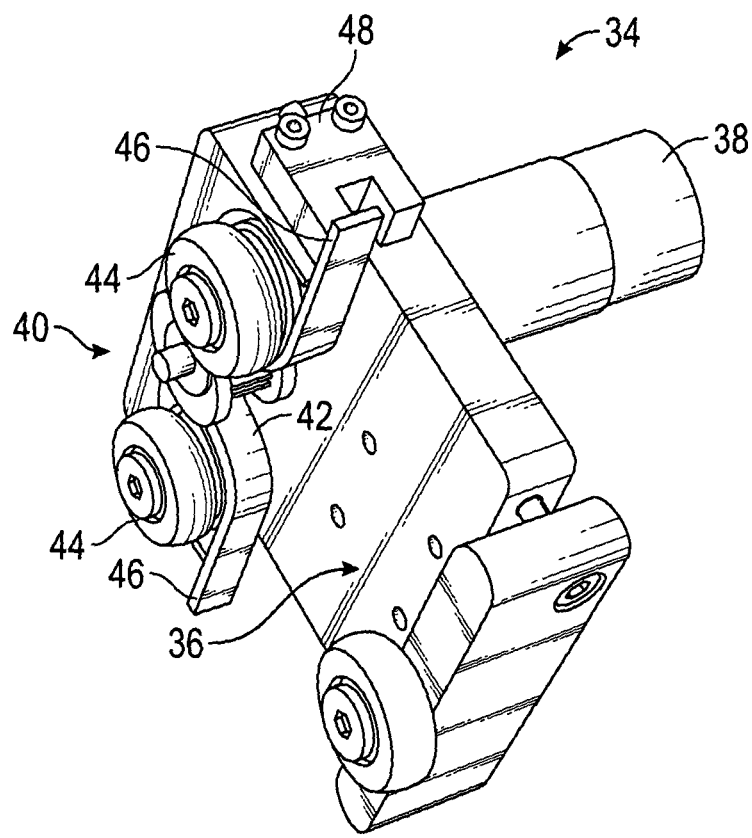

FIGS. 4A-4D and 5A-5B are schematic illustrations of an exemplary rail system 30 of scanner 10 showing the rail 32 and the cart 34. FIGS. 4A and 4B show a top view of the rail system 30 and FIGS. 4C and 4D show a front view of the rail system 30. FIGS. 4A and 4C illustrate the cart 34 coupled to the rail 32 in the rail system 30, and FIGS. 4B and 4D illustrate an enlarged view of the cart 34 (i.e., regions marked G and H) in FIGS. 4A and 4C respectively. FIGS. 5A and 5B are upper and lower perspective views of an exemplary cart 34 of the rail system 30. In the description that follows, reference will be made to FIGS. 4A-4D and 5A-5B. Although not a requirement, in some embodiments, the linear length E (see FIG. 4A) of the rail 32 may be between about 50-170 cm, and it may subtend an angle θ between about 5-180° (around a center of the curved rail). However, it is also contemplated that in some embodiments, the rail 32 may subtend an angle θ greater than 180° (e.g., about 270° or 360°). In embodiments where the angle θ≈360°, the rail 32 may include a hinge that enables portions of the rail 32 to be opened, or separated and reattached, to allow a subject to pass through. In some embodiments, length E may be between about 100-150 cm (or about 124.4 cm) and the angle θ may be between about 60-90° (or about 78°). Although not a requirement, in some embodiments, the linear length E of the rail 32 may be less than the width B (see FIG. 3C) of the housing 12 to enable the rail 32 to be positioned within the housing 12.

The surfaces of the rail 32 may have any configuration that enables the cart 34 to slide on the rail 32. In some embodiments, the rail 32 may have one or more smooth surfaces that the cart 34 slides on, while in other embodiments, one or more surfaces of the rail 32 may have grooves, notches, or other features (not shown) that serve as gripping features for the cart 34 as it slides on the rail 32. These gripping features may be formed directly (e.g., machined) on the body of the rail 32, or may be formed on another body (e.g., part, strip, etc.) which is attached to the rail 32. The rail 32 may be attached to the housing 12 in any manner. In some embodiments, the rail 32 may be attached to housing 12 using fasteners (screws, rivets, etc.) that pass through openings on the top (or any other) surface of the rail 32 (see FIG. 4A).

Cart 34 may be coupled to the rail 32 in any manner that enables the cart 34 to slide on or otherwise move along the rail 32. In some embodiments, one side of the cart 34 (see, for e.g., FIG. 5B) may include a recess or a cavity 36 which may engage with, or fit over, the rail 32 (see FIGS. 4B and 4D). The cart 34 also includes a traction system 40 that enables the cart 34 to move on the rail 32 in response to the rotation of an electric motor 38 provided on the cart 34. The traction system 40 may include a drive pulley 42, one or more roller bearings 44, and belts 46 that collectively operate to move the cart 34 along the rail 32 in response to the rotation of the motor 38. The rotation of the motor 38, rotates the traction system 40, which, in some embodiments, is a shaped gear that engages the grooves on the belt. The turning of the motor 38 in one or another direction will cause the cart 34 to move along the rail utilizing the traction provided by the grooves on the belt. In some embodiments, the electric motor 38 may be a linear DC motor controlled by the computer system 90 through the controller 70. Rotation of the motor 38 may rotate the drive pulley 42, which in turn may rotate the roller bearings 44 that act as wheels on the rail 32 to move the cart 34 along the rail 32. Although a specific type of traction system 40 is described above, this is only exemplary. In general, any known configuration of elements (gears, pulleys, belts, links, etc.) may be used to move the cart 34 on the rail 32 in response to the rotation of the motor 38.

The cart 34 may also include one or more sensors coupled thereto. These sensors may include sensors 48 (see FIGS. 4B and 5B) for detecting a position of the cart 34 relative to the rail 32. In some embodiments, sensors 48 may be positioned on either side of the cart 34 (see FIG. 4B) to detect when the cart 34 has reached the end of the rail 32. In some embodiments, cart 34 may include three position-detecting sensors. For example, cart 34 may include two sensors 48 for detecting when the cart 34 reaches the left and right ends of the rail 32, and another sensor (not visible in FIGS. 4B and 5B) to detect when the cart 34 reaches the center of the rail 32. In some embodiments, one or more of these sensors may assist in stopping the cart 34 at a desired location on the rail 32 (e.g., center of the rail 32) during a scan routine. Although only position-detecting sensors are discussed herein, cart 34 may also include other types of sensors to measure different parameters and provide control of the cart 43 and/or imaging device 20 during scans.

In some embodiments, for example, cart 34 may include sensors that comprise multiple components (e.g., transmitter and receiver), and have infrared (IR) detection capabilities. Some of such sensors may be activated by interrupting the IR signal between the transmitter and receiver. Any type of sensor may be used in cart 34. Although not a requirement, in some embodiments, some of the sensors of cart 34 may have the following capabilities: a sensing range between about 1 mm to about 5 cm (e.g., 5 mm), a minimum sensing object of 0.8×1.8 mm, a hysteresis of 0.05 mm, a supply voltage ranging from 5-24 VDC, 2 outputs (light-ON, dark-ON), a response time under light received condition of 20 µs or less, a response time under light interrupted conditions of 100 µs or less, and/or a response frequency of 1 kHz or more. An exemplary sensor of scanner 10 includes a micro photoelectric IR sensor.

Figure 6A:
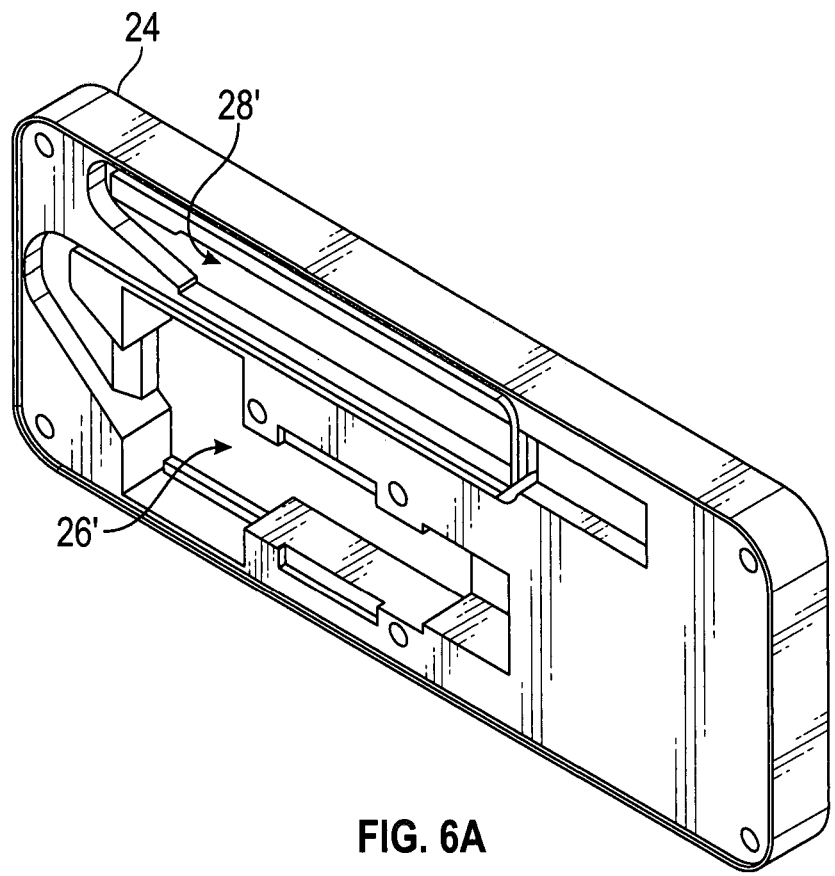
FIGS. 6A-6B illustrate perspective views of two embodiments of an exemplary camera housing of the imaging system of FIG. 1.
Figure 6B:
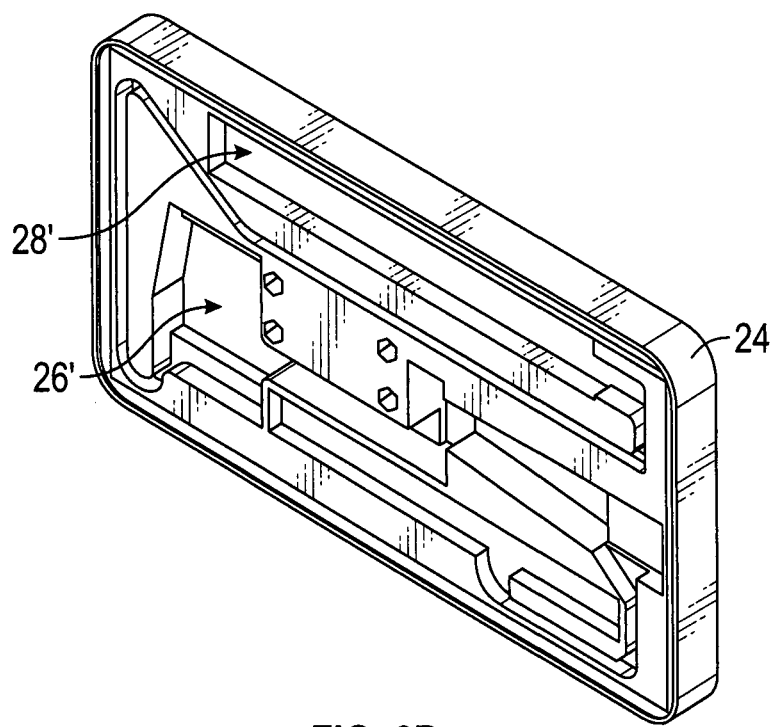

The camera housing 24 may be attached (e.g., removably attached, etc.) to the cart 34 by any method (e.g., using fasteners, mating or locking features, etc.). Typically, the camera housing 24 is attached to a side of the cart 34 that faces the subject positioned in front of the cart 34. FIGS. 6A and 6B illustrate exemplary camera housings 24 that may be used with scanner 10. The camera housings 24 may removably support the one or more cameras 26, 28 (see FIGS. 2C and 3A) of the imaging device 20. In some embodiments, the cameras 26, 28 may be removably attached to housing 24 using fasteners. In some embodiments, a surface of housing 24 that faces the subject may include recesses 26', 28' that mate with corresponding features (e.g., projections) on the cameras 26 and 28 to removably and securely mount the cameras to the housing 24. In some embodiments, the camera housing 24 may be functionally similar to a camera plate used to removably attach a camera to the base of a tripod.

Although a scanner 10 with two cameras is described above, this is only exemplary. In general, the scanner 10 may include any number of cameras (1, 2, 3, 4, etc.). In some embodiments, at least some of these multiple cameras may have different focal points. The use of multiple cameras with offset focal points may provide an enhanced 3-D image display. For example, camera 26 may have a first focal point, and camera 28 may have a second focal point different than the first focal point. Any type of camera may be mounted on the camera housing 24. These cameras 26, 28 may be configured with photo and/or video capabilities to allow for capturing high resolution, high definition image data for generating three-dimensional (3D) images or models. The cameras 26, 28 may include image sensor cameras (e.g., using CCD or CMOS technology, etc.) with any desired resolution for obtaining high quality images (e.g., 1080 p resolution, etc.). In some aspects, the cameras may include infrared capability that provide information relating to depth (e.g., information on the distances between different points on the subject and the imaging device, etc.), relative sizes, and three-dimensional contour of various anatomical features of the subject. This information may assist in better distinguishing the subject from objects in the background. In an exemplary embodiment, one or more cameras 26, 28 mounted to the housing 24 may provide depth information at a resolution 640×480, and color and texture information at a resolution ranging from 960×540 to 1920×1080. In some aspects, the color and texture information may have a resolution of up to 4K. Examples of cameras 26, 28 include, but are not limited to, Intel® RealSense™ camera devices, such as the SR300 and R200. Other non-limiting examples of cameras 26, 28 include form factor cameras that produce .OBJ files, such as Structure Sensor, Microsoft Kinect, and Asus Xtion. In some embodiments, both an SR300 camera and an R200 camera may be mounted on the camera housing 24.

The same or different cameras 26, 28 may be used for scanning various regions of the body. In some embodiments, different cameras may be used for scans of the torso vs. scans of the face. For example, in some embodiments, a first camera (e.g., camera 26) may be used to scan the subject's torso, while a second camera (e.g., camera 28) may be used to scan the subject's face. The color and amount of light provided by the LEDs 36 may be customized for each type of scan. In some embodiments, multiple cameras (e.g., both cameras 26, 28) may simultaneously image the subject during scanning, and image processing routines in the computer system 90 may select the image data to use in creating the 3D image (e.g., based on the quality of the images, noise, etc.).

In some embodiments, the cart 34 may traverse from one side of the rail 32 to the opposite side to produce one imaging scan using the cameras 26, 28. That is, a single scan of the subject may correspond to the images from the cameras 26, 28 during the movement of the cart 34 from a first position on one side of the rail 32 to a second position on its opposite side. In some embodiments, the cart 34 moves from one end of the rail 32 to the opposite end during a scan. That is, in such embodiments, the cart 34 traverses the entire length of the rail 32 during a scan. In other embodiments, the cart 34 traverses less than the length of the rail 32 to produce a scan. The distance that the cart 34 moves on the rail 32 during a scan may be controlled by the computer system 90. In general, the distance travelled by the cart 34 during each scan may be selected based on the application. For example, this distance may be preselected based on the feature being imaged and the size and stature of the subject being scanned.

The computer system 90 may control the position and orientation of the imaging device 20 during a scan. With reference to FIG. 2C, as the cart 34 moves along the rail 32 during a scan, the imaging device 20 moves in the horizontal or the x-direction (or, from one side of the subject to the other). Since the rail 32 is curved, the cart 34 also moves in the y-direction (i.e., towards and away from the subject) as it moves on the rail 32. In some embodiments, the entire rail 32 may also be configured to move into and out of the housing 12 (i.e., in the y-direction) to move the imaging device 20 towards or away from the subject during the scan. In some embodiments, the computer system 90 may move the imaging device 20 vertically (i.e., in the z direction or the height direction of the subject) during a scan by raising or lowering the housing 12 with respect to the base 16. That is, in such embodiments, vertical movement of the imaging device 20 may be accomplished by varying the height of the support member 14. However, it is also contemplated that in some embodiments, the rail 32 may be configured to move vertically independent of the housing 12. In some embodiments, the computer system 90 may be configured to change the orientation of the imaging device 20 by rotating the camera housing 24 (or the cart 34) about the x, y, and/or the z axis during a scan. Such a rotation may enable the imaging device 20 to pivot about an axis (x, y, z, axis, etc.) during the scan.

The position and/or angle of the imaging device 20 may be adjusted by the computer system 90 before, during, or after a scan, to allow for imaging different features of the subject. The imaging device 20 may be controlled to follow any desired trajectory or path during a scan. The trajectory applied in a scan may depend on the application. In general, the trajectory may include translation (or movement) of the cart 34 in one or more of the x-direction, y-direction, and the z-direction, and pivoting of the cart 34 about one or more of the x, y, and the z-axis. In some embodiments, the trajectory of the imaging device 20 during a scan may correspond to translation of the cart 34 from a first location to a second location on the rail 32. However, in some embodiments, the trajectory may be more complex. For example, the trajectory may include a combination of some or all of: horizontal movement of the cart 34 (i.e., along the x axis); vertical movement of the cart 34 (i.e., along the z axis); and movement of the rail 32 (or housing 12) towards or away from the subject (i.e., along the y axis as the cart 34 translates from the first to the second location on the rail 32).

In some embodiments, the trajectory may include moving the imaging device 20 in a repetitive scan cycle as a desired region (e.g., the face) of the subject is imaged. For example, each cycle may include translating the cart 34 from a first end of the rail 32 to a second end (e.g., left to right) at a first rate, moving the housing 12 vertically up or down (i.e., along the z-axis) when the cart 34 is at the second end, and then moving the cart 34 back to the first end (i.e., right to left) at a second rate (i.e., similar to rastering pattern). In general, the second rate may be slower than, the same as, or faster than, the first rate. The cycle may continue until the entire region is imaged.

In some embodiments, the cart 34 may also be rotated or pivoted about an axis as the cart 34 translates on the rail 32. For example, when scanner 10 is executing a facial scan cycle (explained above), the cart 34 may be pivoted up and down (i.e., about the x-axis) and/or left and right (i.e., about the z-axis) as the cart 34 moves along the rail 32. The cart 34 may be rotated in any direction and by any angle during a scanning routine. In some embodiments, the cart 34 may be configured to pivot about the z-axis and about the x-axis by an angle between about 0-45°. Such pivoting may allow the imaging device 20 to face toward the subject as the cart 34 moves on the rail 32. Although, in the discussion above, the cart 34 is described as pivoting, this is not a requirement. Alternatively or additionally, in some embodiments, the housing 12 and/or the camera housing 24 may pivot to vary the angle or orientation of the imaging device 20 during a scan.

As explained above, side to side movement of the cart 34 along the rail 32 may be controlled by the electric motor 38 (see FIGS. 4D-5B). Up and down movement of the rail 32 (or housing 12) may be controlled by one or more motors or actuators (not shown) configured to vary the height D of support member 14 (see FIGS. 3A-3B) in response to commands from the computer system 90. In some embodiments, the up and down movement (i.e., movement along the z-axis) may be controlled by a lifter motor 52 (see FIG. 2C) of the scanner 10. For example, the lifter motor 52 may adjust the height of the housing 12 above the base 16 in response to instructions from the computer system 90. The computer system 90 may instruct the lifter motor 52 to adjust the height of the housing 12 to accommodate the height of different subjects. Additionally or alternatively, in some embodiments, the computer system 90 may activate the lifter motor 52 during the scan process to adjust the path of the imaging device 20 on the vertical axis ellipsis, e.g., to improve the 3D image capture process. Any type motor or actuator may be used as lifter motor 52. Among other types of motors, lifter motors 52 suitable for scanner 10 may include devices made by LINAK US Inc. In some embodiments, the vertical motion of the scanner housing 12 provided by the lifter motor 52 may be automated in a scanning routine. Although not a requirement, in some embodiments, the lifter motor 52 may be positioned within the support member 14 and adapted to move one telescoping elongate part of the support member 14 with respect to another elongate part (to change its length D, see FIG. 3B) as the cart 34 moves along the rail 32.

Movement of the rail 32 towards and away from the subject (i.e., along the y-axis) may also be controlled by one or more actuators (not shown) that are adapted to move the rail 32 in the desired direction in response to instructions from the computer system 90. Alternatively or additionally, in some embodiments, the housing 12 may be adapted to move towards and away from the subject. Pivoting of the imaging device 20 may also be controlled by actuators (or motors) that are adapted to rotate the imaging device 20 by a desired amount about any desired axis in response to instructions from the computer system 90.

In some embodiments, the scanner 10 may also include an RFID reader 50 (see FIG. 2C), or another such sensor, for detecting information embedded in a medical device (e.g., breast implant, etc.) associated with the subject. It should be noted that, although reader 50 is illustrated as being positioned on the imaging device 20, this is only exemplary. In general, the reader 50 may be positioned at any location on the scanner 10. In some embodiments, the reader 50 may be configured to recognize a unique digital identifier (UDI), such as a radio frequency (RF) microtransponder tag or microchip, of a medical device implanted in the subject being scanned. The UDI of a medical implant may include, e.g., serial number(s), manufacturer name(s), date(s) of manufacture, lot number(s), and/or dimensions of the implant. In some embodiments, the UDIs readable by the reader 50 may be included in a sensor incorporated into the implant and configured to detect and/or measure information about the implant and/or the subject. Such sensors may include any of the sensors and/or features thereof disclosed in U.S. Provisional Application No. 62/313,218 filed on Mar. 25, 2016, and U.S. application Ser. No. 15/427,599 filed on Feb. 8, 2017, incorporated by reference in their entireties herein. For example, such sensors may be configured to detect and/or measure one or more of acoustic data, temperature, pressure, light, oxygen, pH, motion (e.g., accelerometers), cyclo-rotation (e.g., gyro sensors), or any other physiological parameter of the subject. Exemplary UDIs that the scanner may recognize also include, but are not limited to, the transponders disclosed in U.S. Application Publication Nos. 2014/0081398 and 2014/0078013, incorporated by reference in their entireties herein.

In some embodiments, the reader 50 may be configured to identify the UDI of a breast implant or other medical implant, and associate that information with the 3D image of the portion of the subject's body that includes the implant generated by the scan. In some embodiments, the reader 50 may be configured to read multiple UDIs for a given subject. For example, the reader 50 may separately identify the UDIs of each of left and right breast implants. The information obtained from the UDIs may be included in a digital profile and/or digital image for the subject (e.g., for registration and validation purposes). In some embodiments, the UDI information obtained by the reader 50 may be received by computer system 90 and further uploaded or otherwise transferred to a local or remote database (e.g., associated with cloud-based network or server). In some embodiments, the subject and/or a healthcare provider may review and/or retrieve the subject's UDI information stored in the database by a suitable electronic device (e.g., computer, smartphone, tablet computer, etc.) for analysis and/or for reference for further services.

With reference to FIG. 1, the computer system 90 (along with its associated software) may control the scanner 10 while scanning a subject, perform image processing of the image data received from the scanner 10, and/or perform simulations on the resulting images. In the description below, although the computer system 90 will be described as performing these and other functions, as will be understood by people skilled in the art, software algorithms running on the hardware components (e.g., microprocessors, etc.) of the computer system 90 may in fact perform these functions. Further, although computer system 90 in FIG. 1 is illustrated as a single desktop computer, this is only exemplary. In general, computer system 90 may include any type of computing devices (e.g., single-board computers, microcontrollers, general-purpose computers, personal computers, etc.). Examples of computing devices that may be used in the computer system 90 may include, but are not limited to, the Intel® Edison microcontroller, the Arduino microcontroller, and the Intel® Next Unit of Computing (NUC). In some embodiments, the computer system 90 may include multiple electronic devices (computers, servers, smartphones, tablets, personal digital assistants (PDAs), etc.) in wired or wireless communication with each other. For example, in some embodiments, computer system 90 may include a computer in direct communication with the controller 70 and multiple other electronic devices (server systems, memory systems storing databases, smartphones, PDAs, etc.) wirelessly coupled to the computer over the interne or other known communication network (LAN, PLAN, etc.).

In some embodiments, computer system 90 may include multiple computational devices configured to perform different specialized functions. For instance, these multiple devices may include a first computer configured as a microcontroller that controls the sensors, actuators, motors, and other scan related systems of the scanner 10, and a second computer that controls the image processing and management (saving, cataloging, retrieving, etc.) aspects of the system. The first computer may include components such as analog digital converters (ADC) and pulse width modulation (PWM) components. In some embodiments, the first computer may include software modules configured to optimize the scanning capabilities of the scanner 10 for different portions of the body (such as, e.g., the torso, face, etc.), and the second computer may include software modules configured to optimize the image processing and data management capabilities. The first computer may communicate with the second computer (e.g., a PC) through one or more communications ports. In some embodiments, the first computer and the second computer may be separate components, while in other embodiments, the first and second computers may be parts of the same computer system.

The computer system 90 may include associated input devices (e.g., keyboard, mouse, touchscreen, etc.) that enables a user (doctor, technician, etc.) to provide input to the computer system 90. Using these input devices, the user may input relevant information of a new subject (name, address, height, weight, dimensions, and other relevant information) into the computer system 90. This information may be stored in a database associated with the computer system 90 (i.e., locally or remotely located) as the subject's profile. The profile of a subject may include any information identifying the subject (e.g., the subject's first name, last name, date of birth) and the type of scan (e.g., torso, facial, other). In some embodiments, the profile may include information on the subject's medical history (e.g., prior medical procedures, medicines taken, etc.), and/or information about any medical implants that the subject may have. For example, the subject profile may indicate whether the subject has any breast implants or other implants or prosthetics, the type of each implant and its location, the implant manufacturer, date of manufacture, warranty information, and/or serial number of each implant. Additionally or alternatively, the patient profile may include medical data such as blood pressure and the existence or absence of any allergies or other medical conditions. The user may view (and modify if needed) the profiles stored in the database. While scanning a preexisting subject (i.e., a subject for whom a profile has already been created), the user may select the subject's profile from the database.

The computer system 90 includes image scan routines (or scanning algorithms) that, when activated, direct instructions to the components of the scanner 10 (imaging device 20, cart 34, LEDs 36, etc.) to perform a scan. These scan routines may include software modules written using any type of computer language. In some embodiments, the scan routines may include one or more application programming interface (API). Exemplary scan routines of computer system 90 will be described in more detail later. Computer system 90 may also include software algorithms or modules configured for processing the image data received from the scanner 10, computation modules configured to extract desired features (dimensions, etc.) from the images, and one or more simulation modules configured to perform the desired simulations (explained further below). Each of these software modules may generate one or more include graphical user interfaces (GUIs) or windows on the display device 92 that enable the user to provide input to the computer system 90. Although the software modules that control scanning, image processing, and simulation are described as being included on the computer system 90, this is only exemplary. In some embodiments, one or more of these modules may be remotely located (e.g., in a cloud server) that may be accessed by computer system 90.

Controller 70 may serve as an interface between the computer system 90 and the components of the scanner 10. For instance, the controller 70 may convert signals between the computer system 90 and the scanner 10 to a form that will be recognized by each component. In some embodiments, the controller 70 may control the movement of the imaging device 20 (translations and/or rotations in the x, y, and z axis) based on input from the sensors (e.g., sensors 48) of the scanner 10. The controller 70 may be configured to control horizontal and vertical translations (and/or rotations) of imaging device 20 simultaneously or in a serial manner. For example, the controller 70 may control left/right movement of the cart 34 on the rail 32 by controlling the operation of the motor 38 of cart 34. Similarly, controller 70 may control the up and down movement of the rail 32 or housing 12 (and/or the pivoting of the imaging device 20 about an axis) by controlling the motors/actuators (of the scanner 10) configured to produce such movements. In some embodiments, the controller 70 may generate and apply pulse width modulated (PWM) signals to control the operations of the scanner 10. The controller 70 may also control the LEDs 36 during a scan. In some embodiments, one or more of the intensity, timing (e.g., when individual, or a set of, LEDs 36 are turned on and/or off during a scan), and power on/off to the LEDs 36 may also be controlled using PWM signals.

In some embodiments, the controller 70 may serve as a standardized hardware component that enables the scanner 10 to operate with different types of computer systems 90 (e.g., smartphone, server system, etc.). In some embodiments, the controller 70 may be custom-made to enhance the capabilities of a specific computer system 90 (e.g., enhance Intel® Edison's capabilities). Although computer system 90 and the controller 70 are described and illustrated as being separate components, this is only exemplary. In some embodiments, the functions of both the computer system 90 and the controller 70 may be integrated into a single component. In some embodiments, communications between the computer system 90, controller 70, and/or the scanner 10 may be through a serial communications link (e.g., using the communication (COMM) ports in a PC's operating system). These serial communications may be provided from the scanner API to the computer system 90 and vice versa.

Although not illustrated in the figures, imaging system 100 may include one or more power supplies configured to provide external electric power to components (scanner 10, controller 70, computer system 90, etc.) of the system. Any type of power supply capable of providing sufficient current and voltage to operate these components may be used. The power supplies may be integral with the components or may be a separate part electrically coupled to the components. Although not a requirement, in some embodiments, an external 24V power supply may be coupled to a peripheral controller, and an external 12v power supply connected to a motor controller, of controller 70. In some embodiments, these external power supplies may be controlled independently, such that they are not connected directly to the controller 70. In some aspects, an external 9V power supply may also be connected to the computer system. In some embodiments, some or all components of the imaging system 100 (e.g., scanner 10, controller 70, computer system 90, etc.) may also include internal power supplies (e.g., one or more batteries) that provide power to these components. The internal power supplies may be used when external power is not available (e.g., blackout, etc.), for example, or is not stable (e.g., voltage fluctuations, etc.). Such internal power supplies may also facilitate transport and/or use of the imaging system 100 in different locations.

The imaging system 100 may be configured to perform any type of scan (facial scan, torso scan, etc.) or a combination of scans on the subject using the scanner 10. The user may request a scan of the subject via the computer system 90. In some embodiments, the user may manually enter the parameters needed for the scan into the computer system 90 (e.g., into a GUI) using an input device (e.g., keyboard, mouse, touchscreen, etc.), and initiate the scan (e.g., by pressing a key on the keyboard, selecting an icon in the GUI, etc.). In some embodiments, various customized scan routines (e.g., facial scan, torso scan, etc.) may be preprogrammed into the computer system 90, and the user may select one of these customized scan routines to scan a subject. These scan routines may prescribe various parameters for the scanner 10 to use while scanning the subject.

Any variable that affects the image captured by the imaging device 20 during the scan may be a parameter. For example, the parameters may include variables that affect the quality of the obtained image, such as, for e.g., color, texture, landmarks, depth, scan type, scanning area (width, height, depth), etc. The parameters may also include the trajectory (e.g., x, y, z translations of the image device, etc.) of the imaging device 20 during the scanning, settings for scan speed (e.g., speed of x, y, z translations, etc.), settings for the LEDs 36 (which LEDs to turn on, when the LEDs are turned on, wavelength(s) of light, etc.), settings for the cameras 26, 28, etc. In some scanning applications, a single scan of a target area of the subject may be sufficient to generate a suitable image, while in other applications, multiple scans may be needed for a suitable image. Therefore, in some embodiments, the scan routine may also define the number of scans to be taken of a particular area, and the variables for use in image processing (e.g., for combining the data obtained from the multiple scans into a single image file).

The imaging device 20 (of the scanner 10) may acquire and display a real-time image of the subject positioned in front of the scanner 10 on the display device 92 of the computer system 90. The user may use this real-time image to adjust the position of the subject in front of the scanner 10 before acquiring images. In some embodiments, the computer system 90 may include features that assist the user in correctly positioning the subject. For example, augmented reality features, such as, lines, grids, or other indicators may be presented on the display, along with the subject's real-time image, to assist the user in correctly positioning the subject. The location of these indicators on the display device 92 may be based on calculations for reference anatomical features of the subject. For example, based on the information (height, dimensions of features, etc.) in the subject's profile, the location of indictors corresponding to relevant facial features (e.g., the brow ridge for a facial scan, sternal notch for a torso scan, etc.) may be calculated, and identified on the display device 92. Using the displayed indicators as a guide, the user may adjust the position of the imaging device 20 (or the subject in front of the imaging device 20) such that the indicators are positioned at the correct location on the subject's image.

The computer system 90 may include any number of customized scan routines that a user may choose from. For example, in some embodiments, a customized software module (AX3) may be provided in computer system 90. The AX3 software module may be configured to perform a scan (e.g., activate and control the scanner to get images from the scanner) and perform image processing and simulations on the resulting images. For example, the AX3 software module may control the scanner API (subroutine) that performs the scan routines to capture the 3D images. In some embodiments, the 3D images may include three files per image. The AX3 module may convert the 3 files of one image to a single file. In some embodiments, the AX3 module may perform profiling TBS (Tissue Behavioral System) where properties such as skin elasticity, muscle and glandular tissue properties are assigned to sections of the image and results computed. In some embodiments, the AX3 module may also enable the user to select a desired implant from a catalog of implants (Implant Catalogue selection) of one or multiple manufacturers (e.g., catalog of Motiva implants), perform simulations, enable automated anatomical measurement, enable the patient to view the results of the analysis (scanned image and/or the expected result of implanting a selected implant on the body) on the display device 92 of the computer system 90.

In some embodiments, the available scan routines are presented on the display device 92 in a manner that enables the user to select one for application on a subject. The chosen scan routine may be used to image the subject without modification, or the user may modify the parameters associated with a chosen scan routine before initiating the scan. In some embodiments, the computer system 90 may have different APIs for different scan routines. For example, the display device 92 of the computer system 90 may list the available scan routines (e.g., torso scan, facial scan, full body scan, etc.), and allow the user to select the desired scan routine. The computer system 90 may then execute the API associated with the selected scan routine.

Figure 7:
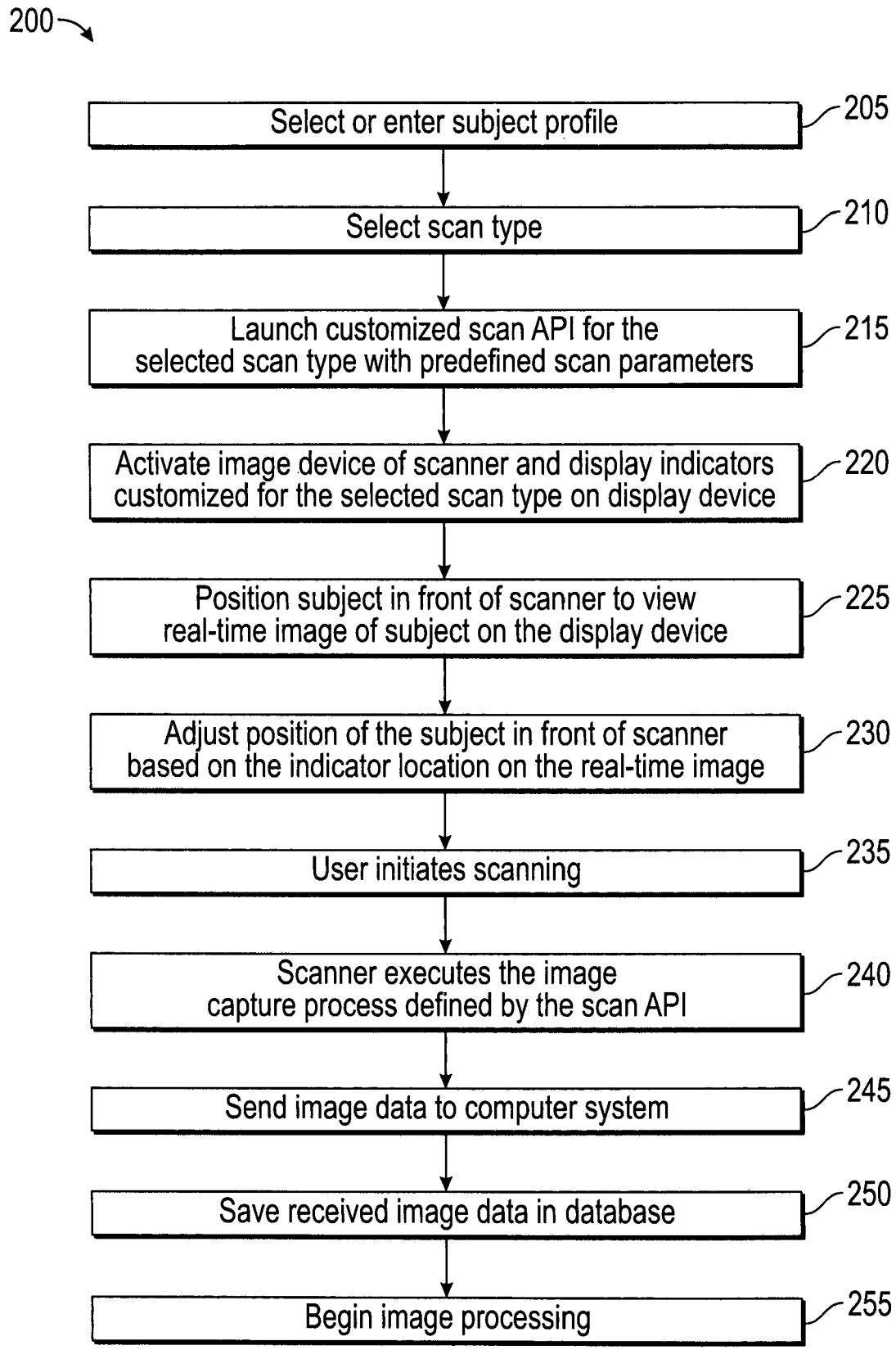
FIG. 7 is a flow chart that illustrates an exemplary method of scanning a subject using the imaging system of FIG. 1.
Figure 8:
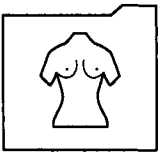
FIG. 8 is an exemplary prompt generated by the imaging system of FIG. 1.

FIG. 7 is a flow chart that illustrates an exemplary method 200 of scanning a subject using a customized scan routine. The method 200 may include all or some of the steps shown in FIG. 7 and/or may repeat certain steps. The user may first select or create the subject's profile on the computer system 90 (step 205). In some embodiments, the names of existing subjects (e.g., clients or patients) may be presented on the display device 92, and the user may click on the subject's name to select the subject's profile. If there is no existing profile for the subject (e.g., no prior scans of the subject have been done), a new subject profile may be entered into the computer system 90 using an input device (e.g., keyboard, mouse, touchscreen, etc.). FIG. 8 illustrates an exemplary prompt generated by the computer system 90 for adding a new subject profile. After entering and saving the subject's profile (name, date of birth, etc.), the user may begin a scan.

In some embodiments, a pop-up window (or GUI) asking whether the user wants to begin a new scan or view on old scan (e.g., view the images associated with a previous scan) may be presented to the user. The user may begin a new scan by clicking an associated icon on the display device 92 (e.g., by clicking on icons labelled "begin new scan," and "OK"). In some embodiments, the computer system 90 may prompt the user to confirm the prior selection. For example, a pop-up window asking "do you want to perform a scan?" may appear on the display device 92, and the user may click "yes" to continue with a new scan. The computer system 90 may then query the user to select the scan type (step 210). For example, the user may presented with a pop-up window with a list of customized scan routines programmed into the computer system 90 (e.g., torso scan, facial scan, full body scan, etc.). Upon selection of the desired scan type, the computer system 90 may launch the scan API associated with the selected scan type with default (or preprogrammed) values for any parameters required by the scan API (step 215). These parameters may include the width, height, and depth of the imaging area, the lighting pattern (LED lighting pattern to achieve a desired cool/warm lighting pattern), intensity of lights, etc. For example, if the user selects "torso scan" as the desired scan type (i.e., in step 210), the scanner API for torso scan is launched (in step 215) with default values for the parameters needed by the API. In some embodiments, the user may change the default values of the parameters in the API (e.g., through a GUI). For example, the API may include a set of predefined lighting patterns (e.g., different combinations of yellow and white LEDs based on the skin tone of the subject), and intensity of lighting, and the user may select an appropriate lighting pattern and intensity for the subject.

The launched scanner API then activates the imaging device 20 and the LEDs 36 of the scanner 10 and display indicators (e.g., augmented reality target lines) associated with the selected scan type on the display device 92 of computer system 90 (step 220). The lighting pattern (combination of white and yellow LEDs) and the intensity of the LEDs 36 may also be adjusted based on the parameters for the selected scan type. The user then positions the subject in a scanning area in front of the scanner 10, and the computer system 90 displays a real-time image of the subject (e.g., acquired using one or more cameras 26, 28 of the imaging device 20) on the display device 92 (step 225). If the displayed indictors are not located at the appropriate locations of the subject's real-time image, the user may adjust the relative position of the subject with respect to the imaging device 20 (step 230). For example, if the indicator for the sternal notch does not overlap with the image of the subject's sternal notch (on the display device 92), the imaging device 20 and/or the subject may be repositioned until the indicator and the image overlaps.

In some embodiments, if vertical (up/down) adjustments are required for the indicator and the image to overlap, the user may click on virtual arrows displayed on the display device 92 to move the imaging device 20 vertically. In some embodiments, clicking on the virtual arrows may send a signal to the controller 70, to activate the lifter motor 52 (of the scanner 10) to move the imaging device 20 in a vertical direction (up or down). If horizontal adjustments (left/right or forward/backward) are required, the user may similarly instruct the controller 70 to move the imaging device 20 left/right or forward/backward. Alternatively or additionally, in some embodiments, the user may instruct the subject to move left/right or forward/backward for proper positioning of the subject with respect to the imaging device 20.

After the subject is properly positioned (in step 230), the user initiates the scan routine in the computer system 90 (step 235). In some embodiments, the user may click on a "start scanning" button/icon of a GUI to initiate scanning. When the user initiates the scan routine (in step 235), the computer system 90 executes the instructions encoded in the scanner API launched in step 215. In response to these instructions, the scanner 10 executes the image capture process defined by the scanner API (step 240). In some embodiments, the scanner API may send instructions to the controller 70 (e.g., using serial communications) to start the selected scan type. These instructions may prescribe a trajectory (including instructions for x, y, and/or z translations, rotations about the x, y, and/or z axis, arc length, number of repetitions, etc.) for the imaging device 20, and instructions for the LEDs 36 (e.g., to activate and vary the wavelength, intensity, etc. at appropriate times during the scan routine, etc.) during the image capture process.

In some embodiments, the prescribed trajectory for a scan may include moving the imaging device 20 in a substantially rectangular pattern. For example, with reference to FIG. 2C, if a facial scan is selected step 210, imaging device 20 (e.g., the cart 34) may first be moved from the center of the rail 32 to one end (e.g., left end) of the rail 32. The imaging device 20 may then be moved down (or up) by a predetermined distance. The predetermined distance may be any value. In some embodiments, this predetermined distance may vary with the type of scan selected. For example, the predetermined distance may be about 15 cm for a facial scan and 20 cm for a torso scan, etc. The imaging device 20 may be moved up or down by moving the housing 12 using lifter motor 52 (see FIG. 2C). In some embodiments, the imaging device 20 may be moved by the predetermined amount by activating the lifter motor 52 for a predetermined time. For example, activating the lifter motor for about 1-5 seconds, e.g., about 2.5 seconds, may move the housing 12 up or down (in a direction transverse to (i.e., extending in a cross direction, not parallel), or substantially perpendicular to, the direction of rail 32) with respect to the base 16 by about 5-30 cm, e.g., about 15 cm. The imaging device 20 may then be moved to the opposite end of the rail 32 (i.e., from the left to the right). While at the opposite end, the imaging device 20 may be moved up by the predetermined distance, and then moved back to the center of the rail 32.

In some embodiments, the imaging device 20 (and/or a camera) may be rotated by a predetermined degree about an axis (e.g., x-axis, z-axis, etc., see FIG. 2C) as the imaging device 20 moves on either side of the center of the scanner 10. For example, in some embodiments of a facial scan, the imaging device 20 may be pivoted or rotated by $\theta_1$ degrees (e.g., about 5-30° (or about 10-20°) from the xz plane) about the z-axis (i.e., left side of the imaging device 20 in FIG. 2C moves out towards the subject as compared to the right side) as the imaging device 20 moves from the center to the left end of the rail 32 and from the left end back to the center, and by $-\theta_1$ degrees (from the xz plane) as the imaging device 20 moves from the center to the right end of the rail 32 and back to the center. Pivoting of the imaging device 20 in the above-described manner may enable obscured features, such as the ears, to be clearly imaged. In a similar manner, in some types of a facial scan (e.g., chin scan), the imaging device 20 may be pivoted about the x-axis (bottom edge of the imaging device 20 moves out towards the subject as compared to the opposite edge or vice versa), as the imaging device 20 moves above or below the center (or the left or right of the center) to image obscured features of the chin. The imaging device 20 may be pivoted about a particular axis based on the type of scan being performed. In some embodiments, the imaging device 20 may not be pivoted (e.g., for some scan types).

In some embodiments, the lighting pattern and/or the intensity of the LEDs 36 may remain the same during an entire scan. That is, the scanner API may select a lighting pattern based on the characteristics of the subject and the selected scan type, and the selected lighting pattern may be kept a constant while the imaging device 20 completed its entire trajectory. However, in some embodiments, the scanner API may prescribe a varying lighting pattern. For example, a first lighting pattern may be applied when the imaging device 20 is moving from the center to the left of the rail 32, and another lighting pattern may be applied when the imaging device 20 is moving from the center to the right of the rail 32. In some embodiments, before image capture, the imaging device 20 of scanner 10 may detect the amount of external light and/or the skin tone of the subject. This information may then be compared to reference information (e.g., tabulated information on lighting conditions suitable for different skin tones) to optimize the lighting conditions. Based on this information, the computer system 90 may turn on a particular combination of colors (e.g., yellow and white) of LEDs 36, and control the intensity of the LEDs 36, to optimize lighting conditions prior to and/or during the execution of a scan routine.

During the image capture process, one or both the cameras 26, 28 of imaging device 20 may be activated, and the imaging device 20 moved along the prescribed trajectory to capture images of the subject from different orientations or viewpoints. In some embodiments, both the cameras 26, 28 may be activated during the scan. In some embodiments, the camera 26 or 28 that is activated may depend on the selected scan type (in step 210). For example, in some embodiments, only camera 26 (e.g., R200 RealSense™ camera) may be activated for a torso scan. When scanning is complete, the controller 70 may send instructions to the scanner 10 to stop the scan process. In some embodiments, the scanner 10 may automatically stop scanning after completing all the instructions in the scanner API launched in step 215.

The scanner 10 then sends the acquired image data to the computer system 90 (step 245). In some embodiments, the computer system 90 may receive the image data from the imaging device 20 in a real-time manner (i.e., as the scan is occurring). In some embodiments, the imaging device 20 or the controller 70 may buffer (or store) the real-time image data and send the buffered data to the computer system 90 in a periodic manner or at the end of the scan. When the computer system 90 receives the image data from scanner 10 (e.g., .OBJ, .MTL, .PNG files, explained later), the files are saved in a database (locally or remotely located) and associated with the subject's profile (step 250). In some embodiments, after completing a scan, the computer system 90 may create a 3D image of the subject's scanned feature (torso, face, etc.) by reconstructing the image from the received image data, and display the reconstructed image on the display device 92 for the user to view. In some embodiments, the computer system 90 may also prompt the user to indicate whether the user wishes to repeat the scan. For example, a pop-up message, such as, for example, "are you satisfied with the scan?" may be displayed on the display device 92. If the user selects "no," the system launches the scanner API again to repeat the scan. If the user selects "yes," the image processing process may start in computer system 90 (step 255).

Computer system 90 may process the image data from the scanner 10 to create a 3D image (or digital 3D model) of the subject's scanned feature(s), and prepare the 3D image for simulations. The computer system 90 may retrieve and process image data saved in the database, or may process the image data as they are received from the scanner 10. In some embodiments, image processing may include converting separate image data files into a single file that contains all the data to produce the 3D image. For example, the imaging device 20 of the scanner 10 may collect and save image data in different file formats. These file formats may include an OBJ file, a MTL file, and a PNG file (e.g., a files having extensions of .OBJ, .MTL, and .PNG, respectively), and/or other data in other file formats suitable for storing, transferring, and/or transmitting image data.

In the example wherein the 3D image is reconstructed from OBJ, MTL, and PNG files, the OBJ file may include mesh data for the 3D image. This file may include some or all the volumetric information for reconstructing the 3D image of the scanned feature. The PNG file may include information regarding texture and color, for example, of different regions of the scanned feature. And, the MTL file may include the configuration information (e.g., the relationship between the PNG and OBJ files). For example, for a facial scan, the PNG file may contain details related to color, texture, etc. of the skin in different regions (bridge, tip, etc.) of the subject's nose. In some embodiments, the MTL file may include the coordinates for proper alignment of the 3D mesh and colors/textures to produce a 3D image. The PNG file may include texture and color information for the scanned subject. In some embodiments, the PNG file format may support eight-bit palletted images (with optional transparency for some or all palette colors), and 24-bit truecolor (16 million colors) or 48-bit truecolor with and without alpha channel (for comparison, the GIF file format generally supports only 256 colors and a single transparent color).

In some embodiments, image data obtained by the scanner 10 (e.g., OBJ, PNG, and MTL files) may be converted to a single file in an AX3 format (e.g., file having a file extension of .AX3) by computer system 90 (using software). The AX3 file may store the image data in a hexadecimal format and may have a file size substantially smaller than a total size of the original three files (e.g., about 5-10 times smaller). In some embodiments, the AX3 file may convert and compress the data for storage as a hexadecimal Binary Large OBject (BLOB). BLOB is a collection of binary data stored as a single entity in a database. Storing the data as BLOB enables the storing of large amounts of information in the database. In some embodiments, AX3 file may be created by the computer system 90 using software ("AX3 software") configured to combine multiple image files into the AX3 file type. For example, computer system 90 may include an Intel® Next Unit of Computing (NUC) with AX3 software. The AX3 file may contain some or all the information necessary to generate a 3D image of the scanned feature. For example, the AX3 file may combine and store data from the OBJ, MTL, and PNG files, each of which includes a different type of image related information.

In some embodiments, the AX3 software, or other suitable software, may combine (e.g., concatenate) the mesh, material, and texture data in a specific order to create the AX3 file or other similar file. In some exemplary embodiments, the OBJ file may be concatenated with the MTL file, and the combination of these two files may then be concatenated with the PNG file to create the AX3 file. For example, OBJ+MTL→OBJ.MTL, and OBJ.MTL+PNG→OBJ.MTL.PNG (or the AX3 file). However, this is only exemplary. In general, the AX3 software may combine the mesh, material, and texture information from the image data in any manner to create a single AX3 file which includes all the information required to create a 3D model. The AX3 file may then be stored in a database. In some embodiments, the AX3 software may interact with the scanner API for initiating and/or terminating different scan routines and other operations of the scanner 10. In some embodiments, the AX3 software may accept instructions from a user (for e.g., entered using an input device of computer system 90). It should be noted that, combining the files from scanner 10 is only exemplary. In some embodiments, the image files from scanner 10 may be directly (i.e., without combining) used to create a 3D image.

The computer system 90 may recreate and display a 3D image (or digital 3D model) of the scanned feature using the AX3 file (or other similar imaging file), and display the image on the display device 92. The computer system 90 may then prompt the user to identify or mark various anatomical features relevant to the area of the subject's body featured in the displayed 3D image. In some embodiments, the computer system 90 may display different views of the digital 3D model on the display device 92 in sequence, and prompt the user (e.g., using a GUI or one or more pop-up windows) to mark (or otherwise identify) relevant anatomical features on the displayed images. In some embodiments, the relevant anatomical features that a user is prompted to identify may be preprogrammed in computer system 90 for different types of scan types. In some embodiments, the user may select a location on the displayed image (e.g., by clicking the location on the screen using a mouse, touchscreen, or other suitable input device) and/or mark (e.g., by inputting text) the selected location as an anatomical feature.

Figure 9:
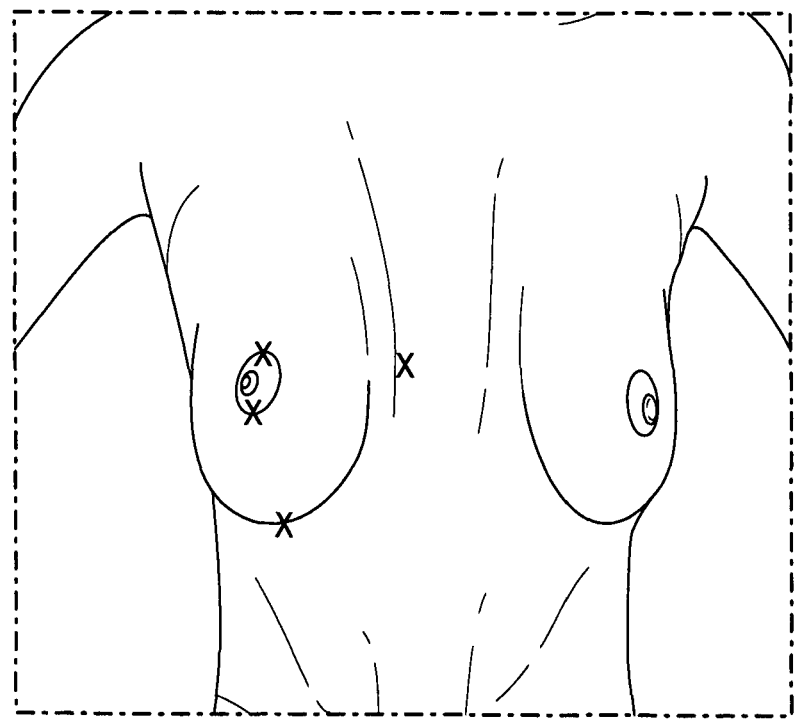
FIG. 9 is an illustration of an exemplary image displayed in the imaging system of FIG. 1 during a torso scan.

FIG. 9 illustrates an exemplary image from a torso scan of a subject indicating some of the anatomical features marked by the user on the image (marked "X" in FIG. 9). The computer system 90 may first display an image of the torso and prompt the user to mark (or otherwise identify) the location corresponding to a selected feature (e.g., right lateral) on the image. Text in a pop-up window (or any other known technique) may be used to prompt the user to identify the queried location. The user may then use a mouse, touchscreen, or another input device to identify this location on the displayed image. For example, in response to the prompt to identify the right lateral, the user may use a mouse to drag a cursor to the appropriate location on the displayed image, and click at that location, to mark this location as the right lateral, or may mark the location on an interactive touchscreen. The computer system 90 may associate the identified location as the right lateral. The computer system 90 may then prompt the user to identify the next feature (e.g., right bottom), and display an image oriented in a manner than enables the user to easily identify the queried location (i.e., the region of the torso comprising the queried location is easily visible to the user).

In a similar manner, the computer system 90 may prompt the user to identify different anatomical features (e.g., all features that are relevant for the analysis) on the torso. These features may include some or all of right lateral, right bottom, right nipple, right areola radius, right sternum, sternal notch, left sternum, left bottom, left nipple, left areola, left lateral, etc. As each feature is marked by the user, the location of this feature on the displayed images may be indicated with a marker (and/or text labelling the identified feature, in some embodiments) identifying the location. After all the relevant anatomical features are identified or marked, the user-identified locations of all the marked features may be illustrated on an image, and the user may be prompted to approve, change, and/or save the identified locations (e.g., by pressing save, etc.).

In some embodiments, at any time during the feature identification process, the user may be able to correct or modify an identified location. In some embodiments, the user may also be able to change the orientation (rotate, translate, zoom in, zoom out, etc.) of a displayed image on the display device 92 at any step during the feature identification. For example, when responding to a query to mark a particular anatomical feature (e.g., left sternum), the user may rotate the image displayed in the display device to view the image at a different orientation for better visibility of the location, ease of marking, etc. The orientation of the image may be changed in any known manner (e.g., using keys on the keyboard, mouse buttons, a touchscreen, etc.).

In some embodiments, as successive images are displayed, the computer system 90 may calculate and display various parameters, based on the user's input, pictorially or as text on a displayed image (or elsewhere on the display device 92). For example, after the user identifies or marks the right sternum location, the computer system 90 may calculate the volume of the left breast based on the locations of the previously identified features and display this volume on the image (e.g., the next displayed image of the torso). Alternatively, or additionally, in some embodiments, the computer system 90 may identify or highlight an area encompassed by the locations of the previously identified features on the image.

Figure 10:
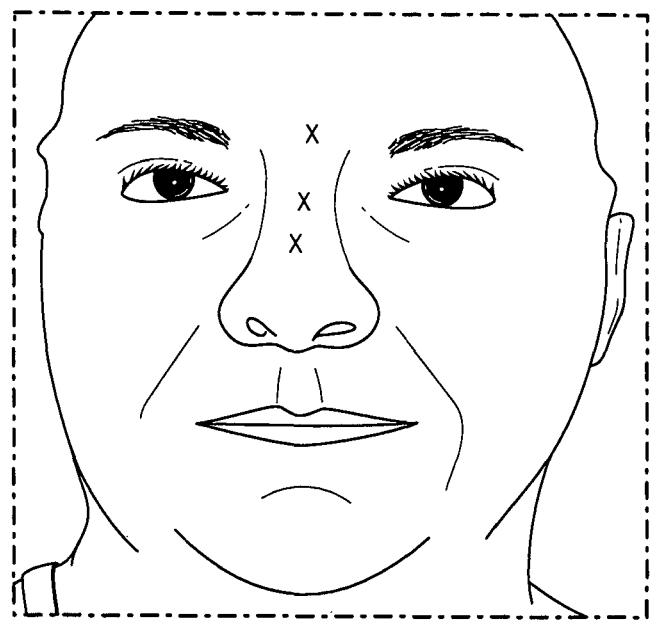
FIG. 10 is an illustration of an exemplary image displayed in the imaging system of FIG. 1 during a facial scan (nose)

FIG. 10 illustrates an exemplary image displayed for marking of anatomical features in a facial scan focused on a subject's nose (i.e., scan type: facial scan—nose mode). As explained with reference to FIG. 9, the computer system 90 may display a 3D image or multiple 3D images of the subject's nose, and prompt the user to identify the locations of the anatomical features that are relevant to a nose scan, on the displayed image. For example, in an exemplary embodiment, the user may be prompted to identify the locations of: nasion, rhinion, supra tip, tip, right tip, right facial groove, columella base, left tip, and/or left facial groove. After these anatomical features are identified, the user-identified features may be displayed on a displayed image, and the user may be prompted to save the selections.

Figure 11:
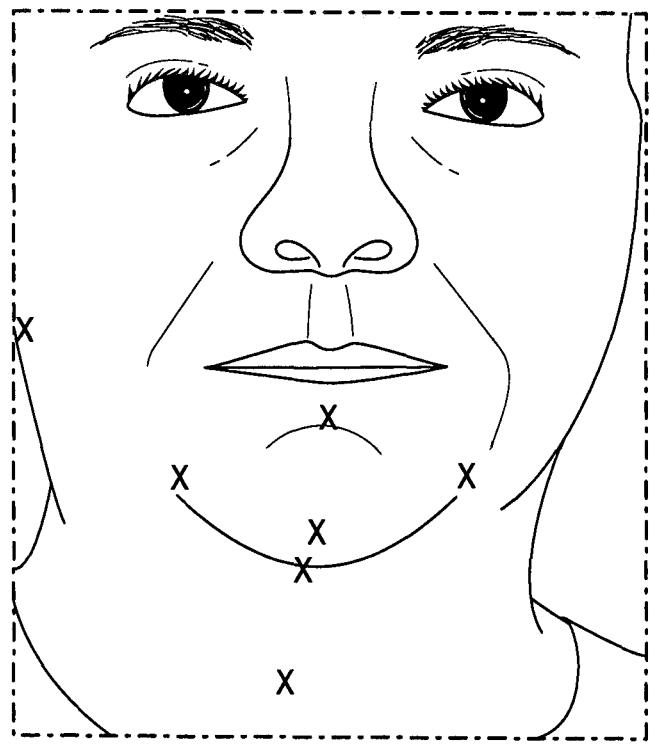
FIG. 11 is an illustration of an exemplary image displayed in the imaging system of FIG. 1 during a facial scan (chin)

FIG. 11 illustrates an exemplary image displayed for marking of anatomical features in a facial scan focused on a subject's chin (scan type: facial scan—chin mode). With reference to FIG. 11, in some exemplary embodiments, similar to the facial scan described above, the user may be prompted to identify different anatomical features related to the chin in an image of the subject's face. These anatomical features may include sulcus, menton, cervical point, right chin, right jaw, left chin, and/or the left jaw. After all relevant anatomical features are identified, the user-identified features may be shown in the an image of the subject's face, and the user prompted to save the selections.

Figure 12:
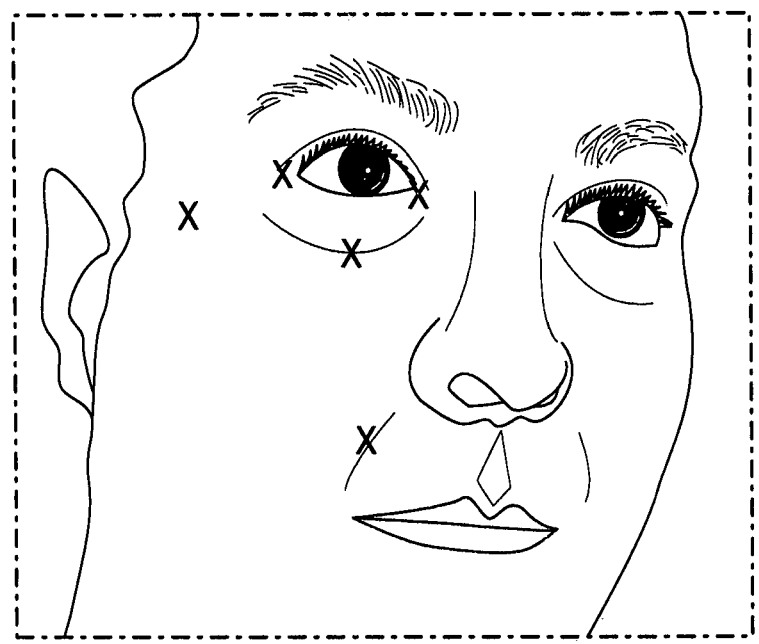
FIG. 12 is an illustration of an exemplary image displayed in the imaging system of FIG. 1 during a facial scan (cheek)

FIG. 12 illustrates an exemplary image displayed for marking of anatomical features in a facial scan focused on a subject's cheek (scan type: facial scan—cheek mode). Similar to the chin scan described previously the user may be prompted to identify anatomical features related to the cheek. In some exemplary embodiments, these features may include some or all of right eye inner, right eye outer, right orbit, right cheekbone lower, right cheekbone rear, left eye inner, left eye outer, left orbit, left cheekbone lower, and/or left cheekbone rear. After all relevant anatomical features are identified, the user-identified features may be shown in the image of the subject's face, and the user prompted to save the selections.

Figure 13:
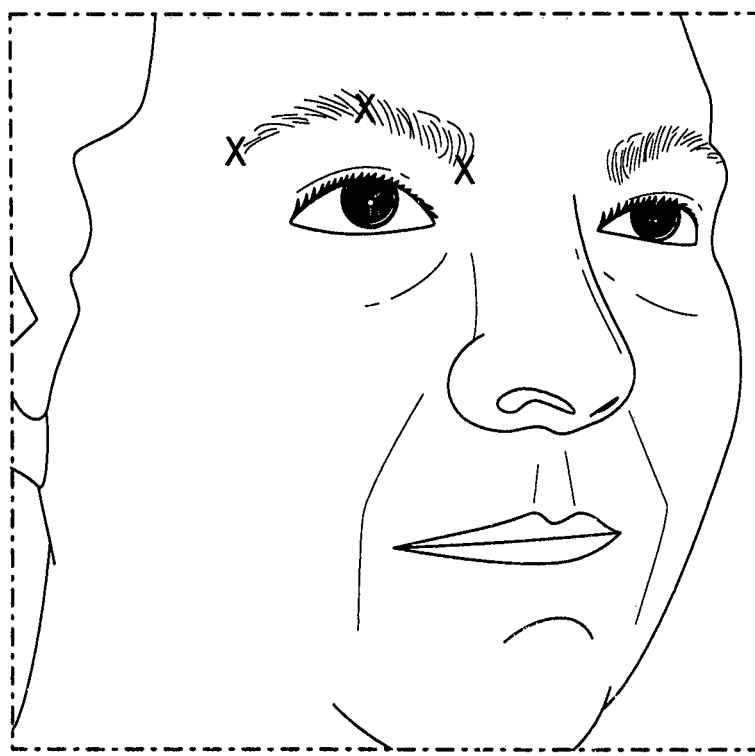
FIG. 13 is an illustration of an exemplary image displayed in the imaging system of FIG. 1 during a facial scan (brow)

FIG. 13 illustrates an exemplary image displayed for marking of anatomical features in a facial scan focused on a subject's brow (scan type: facial scan—brow mode). The user may be asked to identify anatomical features such as right brow inner, right brow outer, right brow upper, right pupil, brow ridge, left brow inner, left brow outer, left brow upper jaw, and/or the left pupil on images of the subject's face. After all relevant anatomical features are identified, the user-identified features may be shown in an image, and the user prompted to save the selections.

It should be noted that the above described anatomical features are only exemplary. Since these and other relevant anatomical features are known to people skilled in the art, they are not discussed further herein. In general, the computer system 90 may prompt the user to identify the locations of any feature or combination of features that may be useful for the simulations (discussed later) that the computer system 90 will perform using the scanned images. In some embodiments, the user may preselect the anatomical features that the user will be prompted to identify for different scan types. Alternatively or additionally, in some embodiments, the location of the anatomical features may be manually entered by the user (e.g., by indicating each feature in the 3D image via a touchscreen, a mouse, or another method of providing user input). For example, the user may click on a location on the 3D image, and type in the name of the anatomical feature corresponding to that location on a window (or a GUI) displayed on the display device 92.

In some embodiments, the computer system 90 may apply algorithms to automatically detect and label various anatomical features that are relevant to a scan type. For example, the computer system 90 may use differences in brightness, color, shapes, patterns, and/or other image characteristics to infer the locations of various features (such as, e.g., the sternal notch, areolas, and nipples, etc., for a torso scan, and the left and right jaw, inner and outer eye, cheekbones, etc., for a facial scan). The user may manually adjust the locations of the auto-generated markers in the image to more closely align with the anatomical feature using a suitable input device. In some embodiments, the computer system 90 may provide suggestions (textual, verbal, highlighted region of the image, etc.) to assist the user in marking the location of an anatomical feature.

Each 3D image and the simulations performed (discussed below) may be saved to a database and associated with the subject's digital profile, so that the saved 3D images and simulations may be accessed at a later date. The database may be a locally-stored database (e.g., in a local memory) or a remotely-stored database (e.g., stored in a cloud-based network or server). The computer system 90 may transmit and receive data from the database wirelessly or using a wired connection to save and access various saved images and simulations. A healthcare provider may be able to access the database and view the images and simulations through a user interface associated with computer system 90. The user interface may be accessed through, for example, a remote computer or a portable handheld device (smartphone, tablet computer, etc.). For example, the subject's physician or other healthcare provider may launch an application (or "app") on a smartphone or tablet device to access the user interface or the database, select a subject, and view the saved information (images, simulations, etc.) corresponding to that subject. The computer system 90, the user interface, and/or the database may implement appropriate security protocols, such as requiring the user to enter logon credentials to limit access to the subject's profiles and to comply with applicable health regulations, such as the Health Insurance Portability and Accountability Act (HIPAA).

Once the markers for the anatomical features relevant to the scan have been associated with a 3D image (as described above with reference to FIGS. 9-13), various simulations (e.g., modifications to the original 3D image) may be performed to allow the user to visualize expected changes in the subject's appearance, for example, resulting from a contemplated implantation or other medical procedure. For example, simulations may be performed to explore the results of a contemplated breast implantation surgery. The following are some exemplary simulations that may be performed by computer system 90. While the following examples relate to breast implants, the present disclosure is not so limited and may include other types of implants (e.g., gluteal implants, calf implants, nose implants, chin implants, etc.) and aesthetic/reconstructive surgeries (e.g., reconstruction surgeries following a medical procedure or surgeries involving changes to facial features). Additional simulations according to the general principles discussed herein are also contemplated and encompassed in this present disclosure.

Exemplary simulations that may be performed by imaging system 100 include, but are not limited to, simulations of breast augmentation, breast reduction, and breast tissue reconstruction. Such simulations may include automatic determination of relevant dimensions or measurements of the subject's torso, and calculation of the subject's existing breast tissue volume. Accounting for the subject's existing tissue may provide for a more realistic representation of how an implant may affect the subject's appearance. Any known type of algorithm suitable for modifying the original 3D image(s) may be used for the simulations. In some embodiments, the calculation of the existing breast tissue volume may employ a filling vectors and vertices algorithm. The vectors and vertices used in the algorithm may be related to the user-identified markers in the 3D image generated from a torso scan (see FIG. 9). Using the markers, the simulation software of computer system 90 may automatically compute various parameters or dimensions (e.g., distance between anatomical features) that may be used in the algorithms that perform the simulations.

Figure 14A:
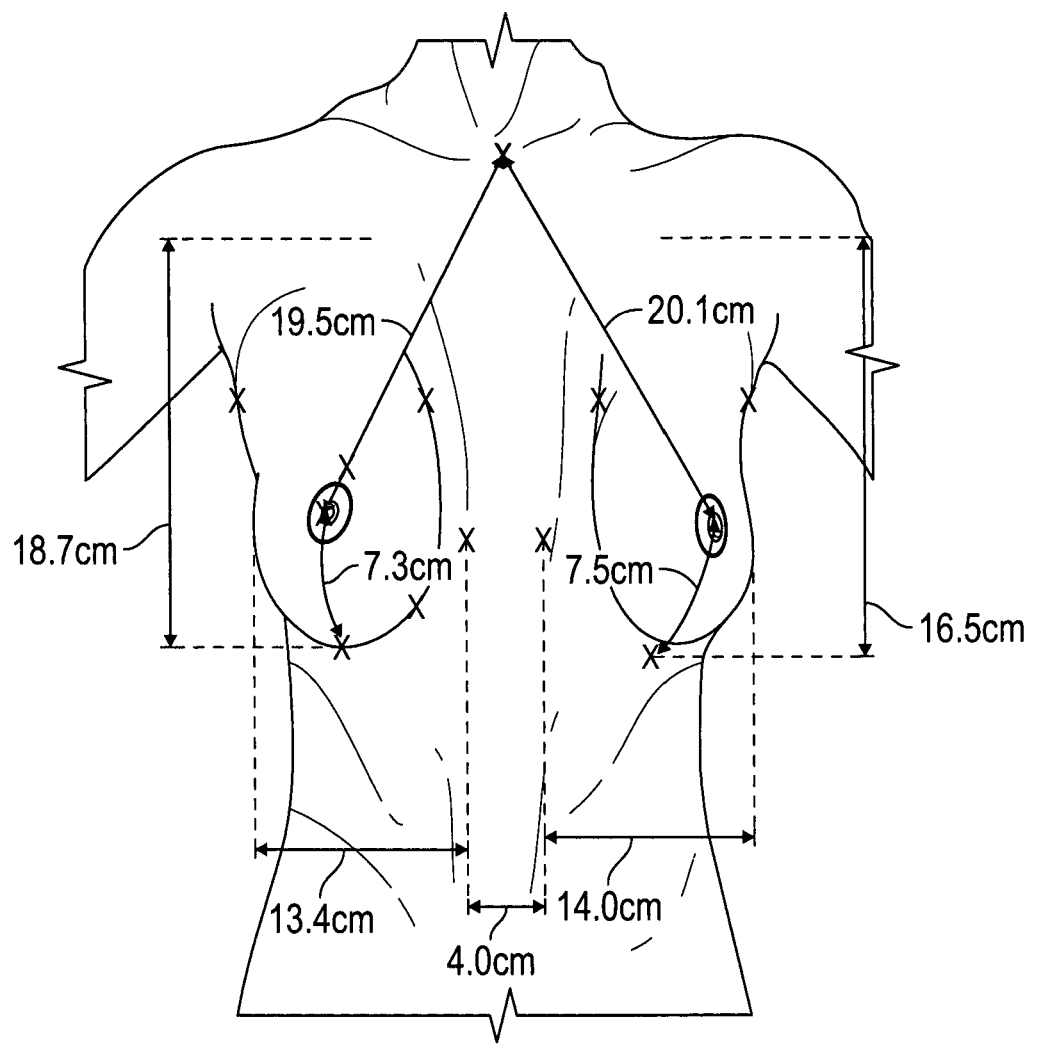
FIG. 14 is an exemplary display by the imaging system of FIG. 1 during image reconstruction.
Figure 14B:
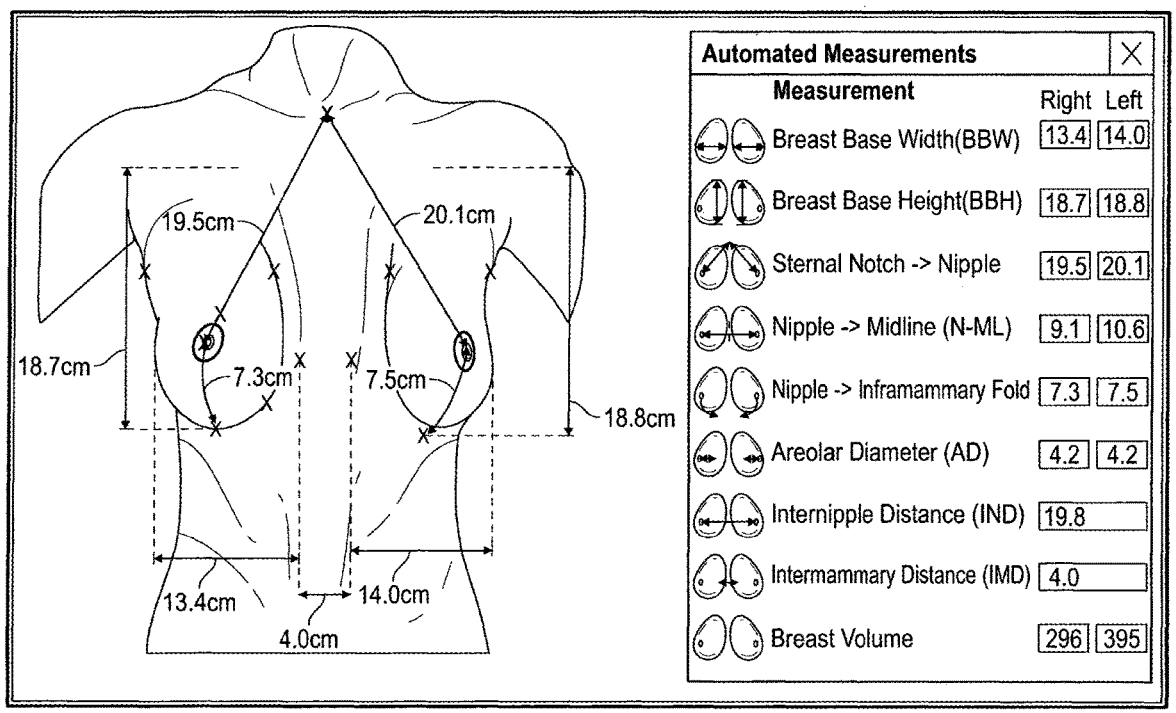

In some embodiments, as illustrated in FIG. 14A, the automatically computed parameters may be pictorially presented on the display device 92. In general, the results of the simulations may be presented in any form. In some embodiments, the simulation results may be presented on the display device 92 (e.g., textually, pictorially, etc.). of the displayed results may include the calculated tissue volume of the left breast and the right breast obtained from a simulation. In some embodiments, as illustrated in FIG. 14B, a summary of the automated measurements, and the calculated values for the tissue volume of the left and right breasts may also be presented on the display device 92.

In some embodiments, the simulation results (e.g., image of a breast with a particular type/size of implant embedded therein) may be presented as a 3D image on the display device 92 of the computer system 90. Using the results of these simulations, the user (and/or the subject) may compare the expected results of different types of surgeries (e.g., the result of implanting different sizes/shapes of breast implants, and/or different placement locations of the implants in tissue) before performing the surgery, to make a more informed choice about a desired surgical procedure. These simulations may be performed by the user, along with the subject, to allow the subject an opportunity to ask questions about the procedure and/or the implants before undergoing the procedure.

It should be noted that the types of simulations summarized above (and described in more detail below) are only exemplary. In general, any type of simulation using a digital 3D model of the subject may be performed by the computer system 90. Although all the described simulations are related to breast implants, this is only exemplary. Analogous simulations may be performed for other types of scans. For example, using the user-identified markers in the 3D images obtained from a facial scan, the computer system 90 may determine the volume of other existing tissues of the subject (e.g., tissues around the chin and cheekbones, etc.). Exemplary simulations that may be performed using a digital 3D image or model of the subject are described below.

Implant revision surgery may involve the removal and/or replacement of an existing implant (e.g., breast implant) from a subject's body. The imaging system 100 of FIG. 1 may be used by simulate, and visualize, the expected appearance of the subject following the surgery before the patient actually undergoes the surgery. In the discussion below, an exemplary case of a subject considering a breast implant revision surgery is described. It should be noted that this case is only exemplary, and the disclosed method is applicable to simulate the effects of any type of implant revision surgery. In an exemplary embodiment, the computer system 90 may perform simulations (e.g., using torso scans of the subject and information about the subject's current implant(s)) to virtually remove an existing breast implant from a digital 3D model of the subject's torso (e.g., a 3D image obtained using scanner 10), optionally add a new breast implant, and display the results on the display device 92. The results may be presented as a digital 3D model and/or a textual display. Based on the simulation, a new 3D model of the subject's torso (i.e., an image without the existing breast implant, optionally with a new breast implant) may be created and displayed on the display device 92, for example, alongside the original digital 3D model (i.e., an image with the existing breast implant) for the user/subject to view and analyze the expected differences. In some embodiments, the results of the simulation may be highlighted (e.g., using different color, shadow, dashed lines, etc.) on the original 3D model of the subject's torso. The computer system 90 may perform additional simulations to visualize the subject with several different types/sizes and/or locations of new implant(s) and present the results on the display device 92.

Information (dimensional details, etc.) about the new implants, required or otherwise useful for the simulations ("implant information"), may be input into the computer system 90 by the user, and/or the computer system 90 may automatically obtain the implant information. For example, in some embodiments, the computer system 90 may communicate with, and obtain the implant information from, a database (e.g., local or remotely located database) that includes details of different types/brands of device used in an implantation procedure, e.g., breast implants and/or tissue expanders. The types of implants populating the database may include, but are not limited to, Motiva Implant Matrix® products (Establishment Labs) and other brands of implants. In some embodiments, the user may enter identifying information (e.g., make and model, serial number, etc.) of a new implant on the computer system 90, and the computer system 90 may download information about the implant from the database. Alternatively or additionally, in some embodiments, based on the identifying information provided by the user, the computer system 90 may access a website associated with the implant (e.g., implant manufacturers website), and download the implant information from the website. In some embodiments, the computer system 90 may display a list of available implants (from the database or saved locally in computer system 90), and the user may select a desired implant from amongst the displayed options.

Figure 15:
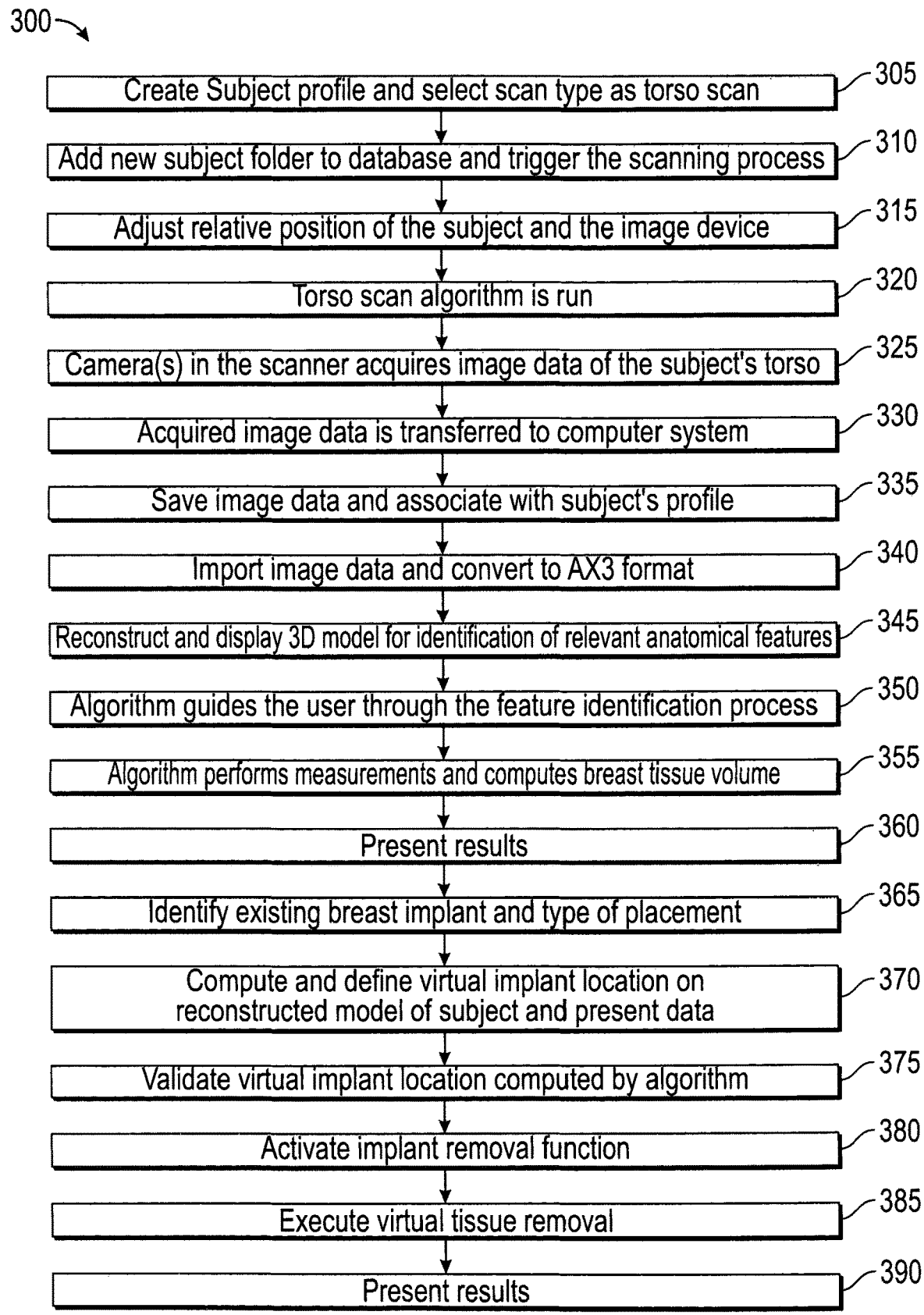
FIG. 15 illustrates an exemplary method of performing breast implant revision surgery simulation using the imaging system of FIG. 1.

FIG. 15 illustrates an exemplary method 300 for performing breast implant revision surgery simulation using the imaging system 100 of the current disclosure. It should be noted that the steps illustrated in FIG. 15 are only exemplary, and one or more steps may be omitted, added, or repeated one or more times to suit the particular circumstances of the simulation and needs or desires of the subject. In the discussion below, reference will also be made to the imaging system 100 illustrated in FIG. 1 and the scanner 10 illustrated in FIG. 2C. A digital profile for the subject is first created by the user using the computer system 90, and the desired scan type is chosen as torso scan (step 305) (see, for example, FIG. 8). The subject's profile is then saved in a database associated with the computer system 90, and the scanning process is triggered (step 310). Alternatively, if the subject already has a saved profile in the database, this profile may be chosen. As explained previously, the display device 92 of the computer system 90 may display suitable data entry windows to assist the user in entering and saving, or selecting, the subject's profile.

Triggering the scanning process (step 310) activates one or more cameras 26, 28 of the imaging device 20 (of scanner 10), and displays the image acquired by the cameras on the display device 92. If the subject is positioned in front of the scanner 10, a real-time image of the subject is also displayed on the display device 92. Indicators (e.g., augmented reality lines, grids, etc.) may also be displayed on the display device 92 to assist the user in properly positioning the subject for image capture. Using these indicators as a guide, the user may adjust the vertical and horizontal position of the subject and/or the imaging device 20 so that the subject is suitably positioned for a torso scan (step 315). In some embodiments, as part of step 315 (as described previously), the user may click on up/down arrows displayed on the display device 92 to move the imaging device 20 vertically relative to the subject, and instruct the subject to move left or right to adjust the horizontal position of the subject with respect to the imaging device 20.

After the subject is suitably positioned, the torso scan algorithm is initiated (step 320). In some embodiments, this step may involve clicking on a keyboard key of (or touch a displayed icon on) computer system 90 to run the torso scan algorithm. As explained previously, among other instructions, the torso scan algorithm may include lines of code that defines the trajectory for the imaging device 20 to follow (i.e., move in) as the cameras 26, 28 acquire image data, and the state (on/off, intensity, wavelength, etc.) of the LEDs 36 when the imaging device 20 is at various points along its trajectory. In accordance with the instructions resulting from the algorithm, one or more cameras 26, 28 of the imaging device 20 acquires image data of the subject's torso as the imaging device 20 moves along the defined trajectory (step 325). In addition to structural/geometrical data of different regions of the torso, the image data may also include color and/or texture information of the different regions. In some embodiments, a RealSense R200 camera may be used to acquire image data during the torso scan. As explained previously, the acquired image data may include multiple files containing data of different types (e.g., OBJ, MTL, and PNG files).

The image data is then transferred from the scanner 10 to the computer system 90 (step 330). In some embodiments, at the completion of the scan, the computer system 90 may automatically upload the image data from the scanner 10. The received image data is then saved in a database and associated with the subject's profile (step 335). In some embodiments, the received image data may be saved in a temporary location. The multiple files of the image data are then imported (from the database or temporary storage space) and converted into the AX3 format (step 340), and then saved in the database. As explained previously, converting the multiple files of the image data into a single AX3 file may reduce the size of the resulting file while retaining substantially all the information contained in the multiple image data files. A digital 3D model (digital body cast) of the subject's torso may then be reconstructed using the image file and displayed in the display device 92 for marking (identification) of relevant anatomical features by the user (step 345) (see, for example, FIG. 9A). Following the prompts provided by the computer system 90, the user identifies the location of the anatomical features in the displayed images. The algorithm may guide the user through the feature identification process by displaying multiple suitably oriented images of the torso with accompanying prompts and tips (step 350) and/or the user may adjust the orientation of one or more images to identify different anatomical features(see, for example, FIG. 9). Based on the locations of the user-identified features, the computer system 90 automatically performs relevant measurements from the 3D image, computes breast tissue volume (step 355), and presents the results to the user (step 360) (see, for example, FIGS. 14A-14B).

The subject's existing breast implant, and type of placement of the implant (sub-pectoral, sub-glandular, etc.), is then identified (step 365). In some embodiments, the computer system 90 may extract this information from the subject's profile, or acquire the information from the embedded implants using the RFID sensor 50 of scanner 10. In some embodiments, the computer system 90 may prompt the user to enter this information (e.g., via pop-up windows, etc.). In some embodiments, the user may be prompted to select the type of implant from a database which includes information about different implants generally available, or from a list of implants presented on display device 92. Based on the information (dimensions, etc.) of the existing implant, the computer system 90 computes or defines a virtual implant in the reconstructed 3D model of the subject's torso, and presents the data (step 370). For example, based on the volumetric and placement information of the subject's existing implant, the computer system 90 may attribute a volume in the reconstructed 3D model as being occupied by the implant, and presents this data to the user. Although the data may be presented in any manner, in some embodiments, the computed existing implant volume and location may be identified in a digital 3D model of the subject's torso displayed on the display device 92. The user then validates the determined implant location (and/or other features of the represented virtual implant), and saves the computed data in the database (step 375). If the user is not satisfied with any aspect of the represented virtual implant, the user may step back through the process, e.g., modify one or more input parameters, and initiate re-computation of the virtual implant (e.g., from step 365).

If the user is satisfied with the represented virtual implant (e.g., step 375), the user may activate the implant removal simulation function in the computer system 90 (step 380). In some embodiments, the user may click on a button or an icon presented on the display device 92 to activate or launch an algorithm (or subroutine) associated with the implant removal function. This algorithm may execute a virtual tissue removal function, and perform simulations that reduce the overall volume of the breast (computed in step 355) by an amount equal to the existing implant volume (obtained from step 365), to simulate the removal of the implant from the breast. The results may then be presented to the user, for example, on the display device 92 (step 390).

Following the simulation of FIG. 15, the user may perform other simulations, such as, for example, simulation of breast augmentation surgery. Breast augmentation is a surgical procedure where a breast implant is placed under the subject's chest muscles or breast tissue to increase the size, shape, or fullness of the breast. Knowing the type of implant that a subject is considering, breast augmentation surgery simulations may create a virtual 3D model of the implant, reconstruct the 3D model of the subject's torso with the implant embedded therein, and present the results to the user (similar to step 370 of FIG. 15). The presented results may include a digital 3D model of the subject's torso (e.g., a modification of the original 3D image obtained using the scanner 10 or obtained as a result of a previous simulation) with the selected implant embedded therein. Based on these results, the subject can decide to go ahead with the surgery or select another implant or placement/orientation information for simulations.

Figure 16:
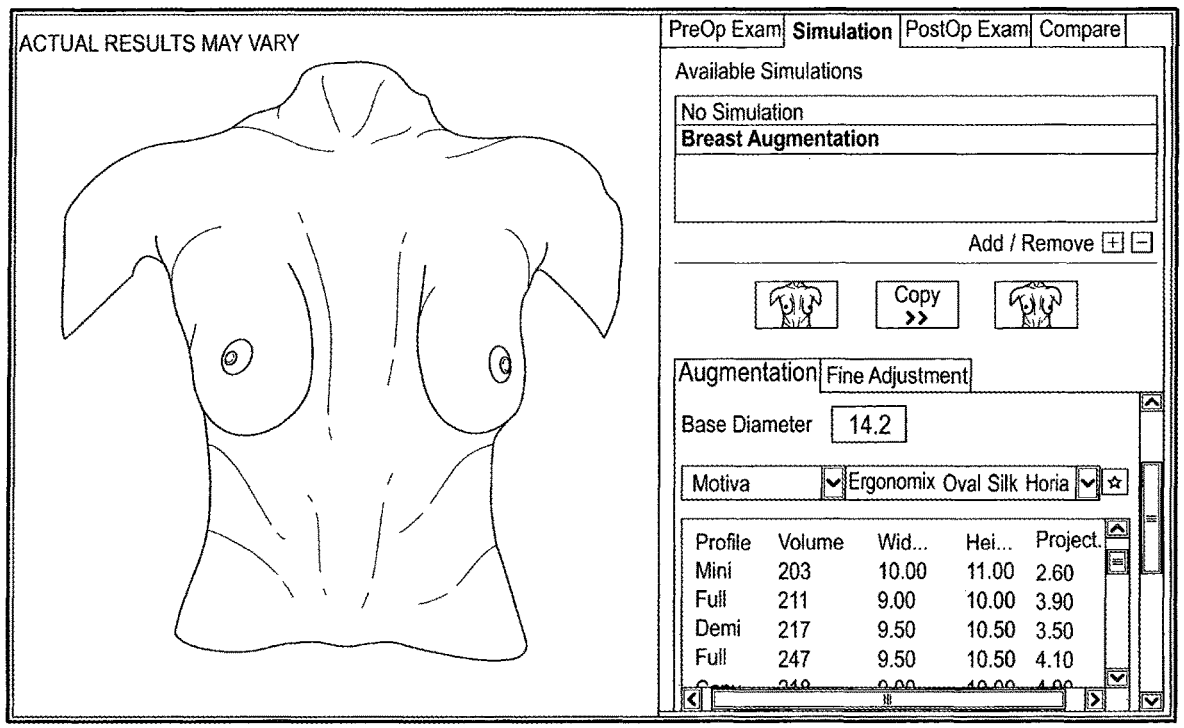
FIG. 16 illustrates an exemplary database with a list of available implants for use with the imaging system of FIG. 1.

In a breast augmentation surgery simulation, the user (or subject) may first select an implant for the simulations and provide details of the implantation procedure (e.g., sub-pectoral implantation, sub-glandular implantation, etc.) to the computer system 90. As explained previously, the details (dimensions, model, etc.) of the implant may be provided by the user to the computer system 90, or the implant may selected from a database that includes details of different types of implants. FIG. 16 is an illustration of a database that includes an exemplary list of available implants (e.g., Motiva Ergonomix™ implants) of varying sizes (e.g., mini, full, demi, corse, etc.). In some embodiments, the computer system 90 may generate a list of implants that takes into account particulars of the subject (e.g., the dimensions of the torso, volume and/or type of existing breast tissue, etc.). For example, the computer system 90 may exclude from the presented list, implants that fall outside a range of implant sizes determined to be suitable for a given subject (e.g., based on defined criteria). The user may select a desired implant from the presented list of available implants (e.g., from the list of FIG. 16). Using details of the implant and the implantation procedure, the simulation algorithm may compute a virtual implant and reconstruct the digital 3D model of the torso with the implant embedded therein. The results of simulations may be presented on the display device 92. The user may review and validate the results, or modify the parameters and initiate re-computation (similar to step 375 of FIG. 15) with the modified parameters.

In general, the effect of any type of tissue/implant/prosthesis removal or addition may be simulated using imaging system 100. In some embodiments, simulations may be performed to visualize and study the effect of breast reconstruction following a mastectomy or partial mastectomy (e.g., due to breast cancer). In addition to breast implants, in some embodiments, the imaging system 100 may be configured to simulate tissue expanders used to prepare chest tissue to receive an implant. For example, the imaging system 100 may perform volumetric calculations that take into account a subject's existing breast tissue, and then allow the user to simulate one or more tissue expanders and/or one or more breast implants following the tissue expanders(s) to be used during breast reconstruction surgery.

Figure 17:
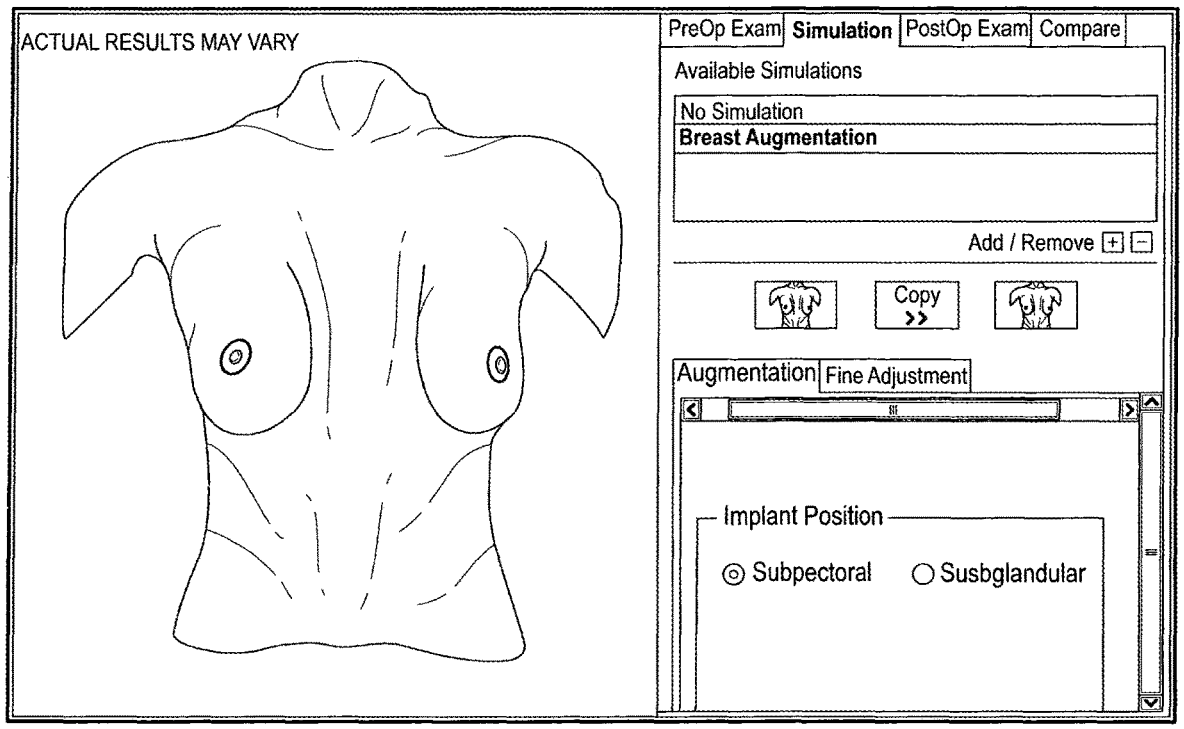
FIG. 17 illustrates an exemplary graphical user interface that allows a user to select the type of implantation during a simulation.

With respect to placement of the implant, the system 100 may be capable of simulating different locations as to where the implant will be placed via different types of implantation procedures. For example, a user may be able to select simulation of a sub-pectoral or sub-glandular implantation of an implant or prosthesis. FIG. 17 shows an exemplary graphical user interface of the computer system 90 that allows the user to select one of two implantation options.

The different simulations of computer system 90 may allow a subject considering any type of implantation surgery to visualize the effect of various implantation options and discuss those options with the user (e.g., a physician). In some sembodiments, the simulations of the type, size, position, and/or location of an implant may be performed using a volumetric or a dimensional algorithm (e.g., based on the user's preferences). Further, in some embodiments, the algorithms used for the simulations may be capable of learning and evolving over time (e.g., via artificial intelligence and/or computational learning). For example, the algorithms may evolve based on comparison of pre-surgery and post-surgery images, stored in a database, to optimize the results of the simulations. In addition, the collection of scans (pre and post-surgery) may provide a dataset to assist in the predictive assessment of outcomes, e.g., according to such parameters as demographics and/or regional preferences.

Figure 18:
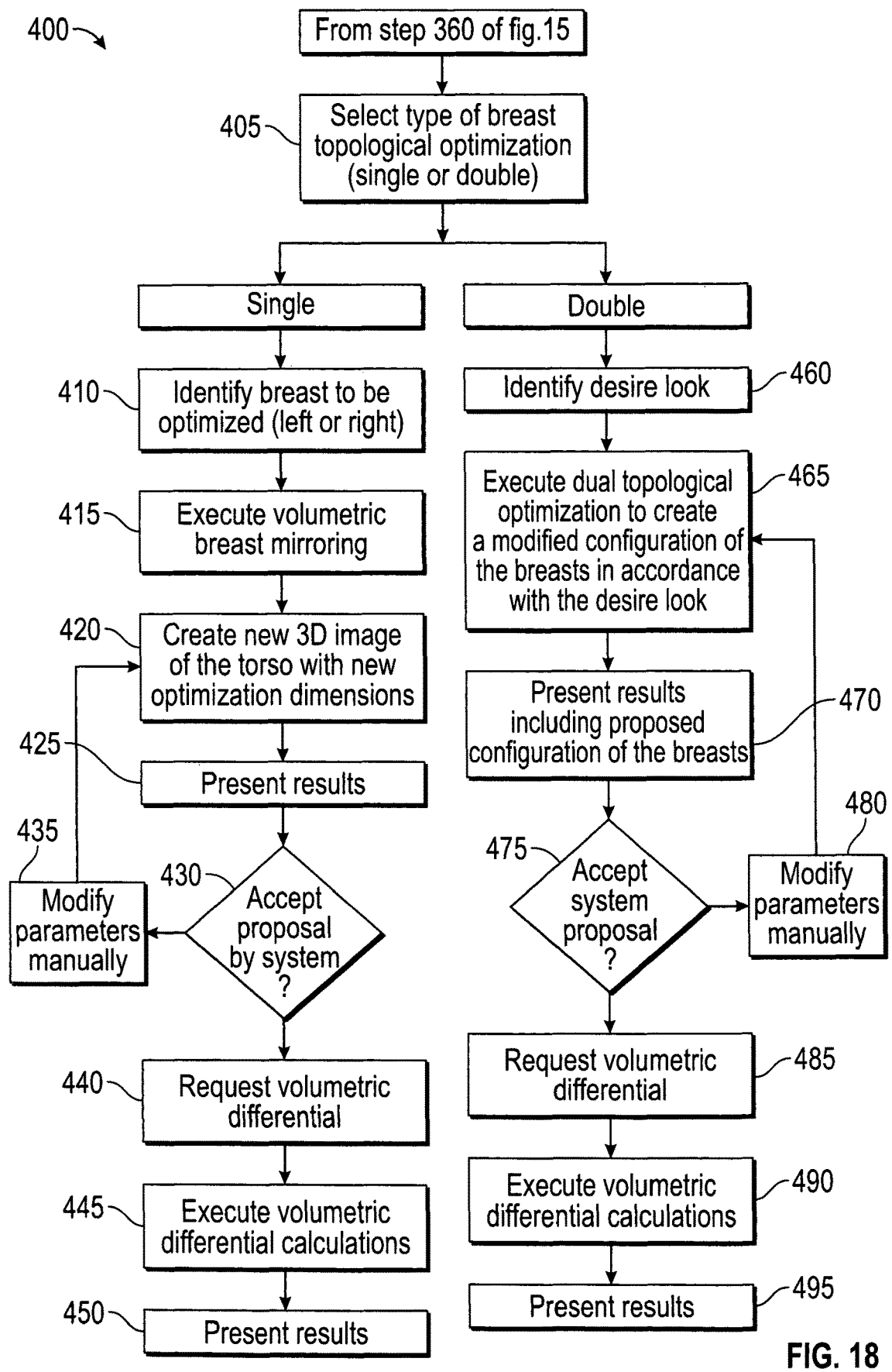
FIG. 18 is a flow chart of an exemplary method for performing breast topological optimization simulation using the imaging system of FIG. 1.

In some embodiments, the imaging system 100 may be used to simulate single or dual breast reconstruction surgeries, for example, to help in planning a surgical procedure. FIG. 18 is a flow chart that shows an exemplary method 400 for performing single and double breast topological optimization simulations. Single breast optimization is used, for example, when only one of the subject's breasts will be modified or reconstructed. In this case, the algorithm may optimize the topology of the breast that is being modified so that the reconstructed topology resembles that of the other (unmodified) breast. Double breast optimization may be used in case both breasts are to be reconstructed, modified, or augmented. In this case, the algorithm may attempt topographical symmetry between the left and right breasts.

Figure 19:
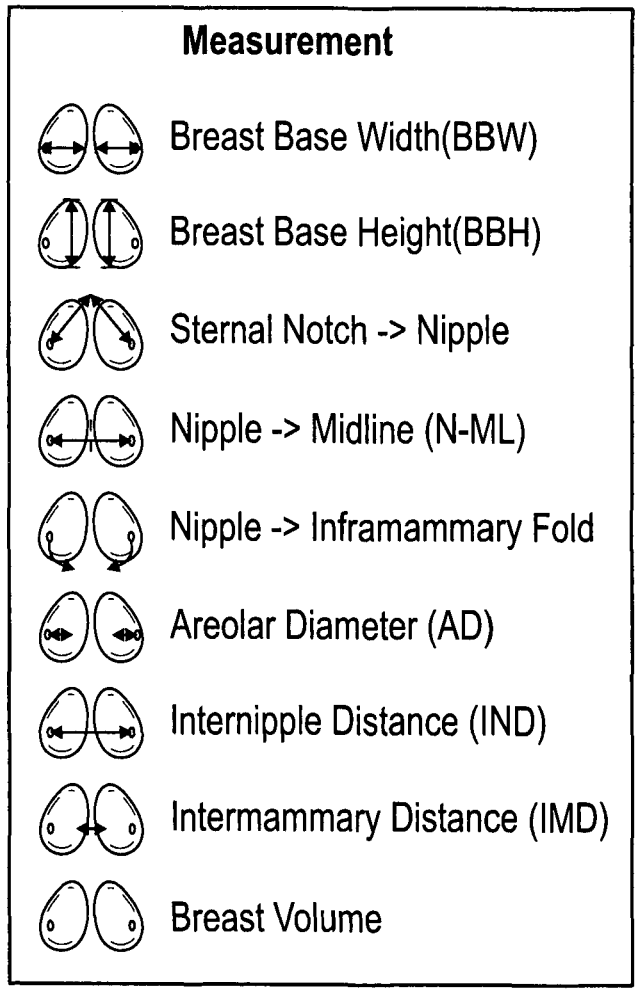
FIG. 19 is a list of parameters used by the imaging system during a simulation.

In a simulation to assist in breast reconstruction surgery, image data of the subject's torso (from the scanner 10 or from the database) is used to reconstruct 3D images of the torso, and compute dimensions and breast tissue volume, similar to steps 305-360 of FIG. 15. The computer system 90 then prompts the user to select the type of breast topological optimization desired (i.e., single or double) (step 405). If the user selects "single," the single breast topological optimization algorithm is activated (left leg of FIG. 18). The user is first prompted to identify the breast (i.e., left or right breast) which is to be optimized (step 410). In response to the user's input, the computer system 90 executes the Volumetric Breast Mirroring algorithm (step 415). This algorithm may perform computations to modify relevant parameters of the target breast (i.e., the left or right breast as chosen by the user in step 415) to the other breast. FIG. 19 is a listing of the parameters that may be used in the volumetric breast mirroring algorithm. Using simulations, the algorithm may modify some or all of these parameters of the target breast to match those of the other (unmodified) breast. The computer system 90 may then compute a proposed topology for the target breast, create digital 3D models/images of the proposed reconstructed breast (step 420), and present the results to the user (step 425). These results may include digital 3D models, dimensions, and other relevant parameters for the reconstructed breast, and represent the system's proposal for the reconstruction.

The user may then be prompted to accept or validate the system's proposal (step 430). If the user does not accept the system's proposal (step 430=No), the user may be prompted to modify the breast parameters (dimensions, volume, etc.) manually (step 435). The algorithm then re-computes the proposed topology for the reconstruction based on the modified parameters (step 420). In some embodiments, the result of step 425 may be manipulated and adjusted by the user. Thus, through simulation, the computer system 90 may suggest a particular topography of the target breast, which then may be adjusted by the user. For example, the computer system 90 may take into account the subject's chest and torso dimensions, and choose one or more implants (or general size categories) to embed in the target breast, when it determines the proposed topology. In some embodiments, in step 435, the user may select a different implant option from a list of available options (e.g., in a database). These options may include different products from one or multiple manufacturers. For example, the options may include different Motiva Implant Matrix® products. Exemplary topological configurations may include (from small to large in size), mini, demi, full, and corse (see, e.g., FIG. 16).

When the user is satisfied with the system's proposal (i.e., step 430=Yes), the user may request the volumetric differential (i.e., the difference in volume and other relevant parameters) between the current topology of the target breast and the proposed topology from the computer system 90 (step 440). Requesting the volumetric differential may include the user clicking on a button or an icon on the display device 92 to initiate volumetric differential calculations. In response to the user's request, the computer system 90 performs volumetric differential calculations (step 445), and presents the results (step 450). These results may include 3D images and other data that illustrate and quantify the volumetric and other differences between the current breast and the reconstructed breast. In some embodiments, when the user indicates acceptance of the system's proposal for the reconstruction (step 430=Yes), the computer system 90 may automatically initiate volumetric differential calculations (i.e., step 445), and present the results to the user (step 450). The user may indicate acceptance of the system's proposal in any manner. For example, by clicking a keyboard key, clicking on/touching an icon on the display device 92, etc.

If the user selects "double" in step 405, the user may be prompted to identify the desired look for the breasts (step 460). Identifying the desired look may include selecting the size/shape or other type of breast (mini, demi, full, corset, etc.) that is desired. The user may indicate this selection in any manner known in the art (clicking on a selection, entering data in a text window, etc.). Based on the user's selection, the computer system 90 executes the Dual Topological Optimization subroutine (step 465). Executing this subroutine may include running an algorithm that computes and creates a modified topography for the breasts with the dimensions of the breasts modified in accordance with the desired look (for e.g., by embedding the selected implant, and matching the dimensions of the two breasts). During these computations, the computer system 90 may access a database that includes predetermined optimal volumes, symmetry ratios, and other data associated with the implants. Results of the computations, which may include digital 3D models of the torso (and/or of each breast) and other relevant results (e.g., dimensions, etc.), may then be presented to the user (step 470). These results may represent the system's proposed topography for the two breasts.

If the user does not accept the system proposal (i.e., step 475=No), the user may be prompted to modify the parameters (e.g., dimensions, volume, etc.) manually (step 480). The algorithm may then re-compute the topography of the breasts with the modified parameters (step 470) and present the results (step 475). In some embodiments, the user may fine-tune or adjust the results of step 470 by modifying one or more aspects of the proposed topography (e.g., symmetry ratio, etc.). When the user is satisfied with the proposed topography (i.e., step 475=Yes), the user may request the volumetric differential in step 485 (i.e., the difference in volume and other relevant parameters between the current breasts and the proposed reconstructed breasts). In response to this request, the computer system 90 performs volumetric differential calculations (step 490), and presents the results (step 495). These results may include 3D images and other data that illustrate and quantify the volumetric and other differences between the current breasts and the reconstructed breasts.

In some embodiments, the computer system 90 may account for additional parameters or practical effects such as human tissue elasticity, implant rheology, implant surface texture, and/or gravitational pull in its simulations. For example, in the breast topological optimization simulations discussed above, the algorithms that perform the simulations (e.g., the Volumetric Breast Mirroring simulations of step 415, Dual Topological Optimization simulations of step 465, etc.) may account for these practical effects for a more realistic result (e.g., simulate the effect of gravity as the torso rotates on the x, y and z axes, etc.). It should be noted that the specific types of simulations discussed above are only exemplary. In general, the computer system 90, and its associated software, may be configured to perform simulations to visualize the expected effect of any type of surgery.

In some embodiments, the computer system 90 may also be used to provide parameters or data that may assist a user in performing a surgical procedure on a portion of the subject's body for which a 3D image is available (e.g., generated by scanner 10 or otherwise transferred to the imaging system 100). For example, algorithms in the computer system 90 may analyze the 3D image and determine one or more parameters (such as, for e.g., incision sites, angle(s) of incision, and the length, width, and/or depth of an incision, etc.) for the surgery. The surgery may include any type of surgery, such as, for example, implantation of a prosthetic device (such as a breast implant, a tissue expander, or other types of implantable medical devices, etc.), addition of tissue (e.g., insertion of tissue or filler materials, etc.), or removal of tissue (e.g., tissue biopsy, removal of a tumor or cyst, liposuction, etc.).

The computer system 90 may provide a number of parameters relevant to a contemplated surgical procedure. In some embodiments, the system may determine an optimal incision site, for example, based on the subject's anatomy and/or the requirements of a given surgical procedure. In some embodiments, the system 90 may generate the surgical parameters based at least in part on user input, a subject profile, and/or reference information for similar types of subjects and/or procedures. For example, the user may specify a sub-pectoral or sub-glandular breast implantation procedure to obtain surgical parameters appropriate for each procedure. Further, for example, a surgeon may need an incision of a certain length (e.g., from about 1 cm to 2 cm, or from about 1.4 cm to 1.8 cm) to insert a breast implant of a particular type or size. The computer system 90 may access this information from a reference database stored locally or remotely for determining different possible locations for an incision of 1.4 cm, 1.5 cm, 1.6 cm, 1.7 cm, or 1.8 cm on one or both breasts shown on a subject's 3D torso scan. To determine appropriate or optimal incision site(s) for the specific patient, the software algorithms of computer system 90 may take into account anatomical features of the subject, such as the size, location, and/or contours of the inframammary fold, areola, tissue volume, etc.

In some embodiments, the computer system 90 may include a software and/or a hardware module that measures and tracks volumetric changes in different body parts as they progress over time (e.g., as the subject ages). This module may track the volumetric changes based on scan data collected at different times. In some embodiments, the module may be configured to simulate liposuction and/or other changes in body contouring.

Figure 20:
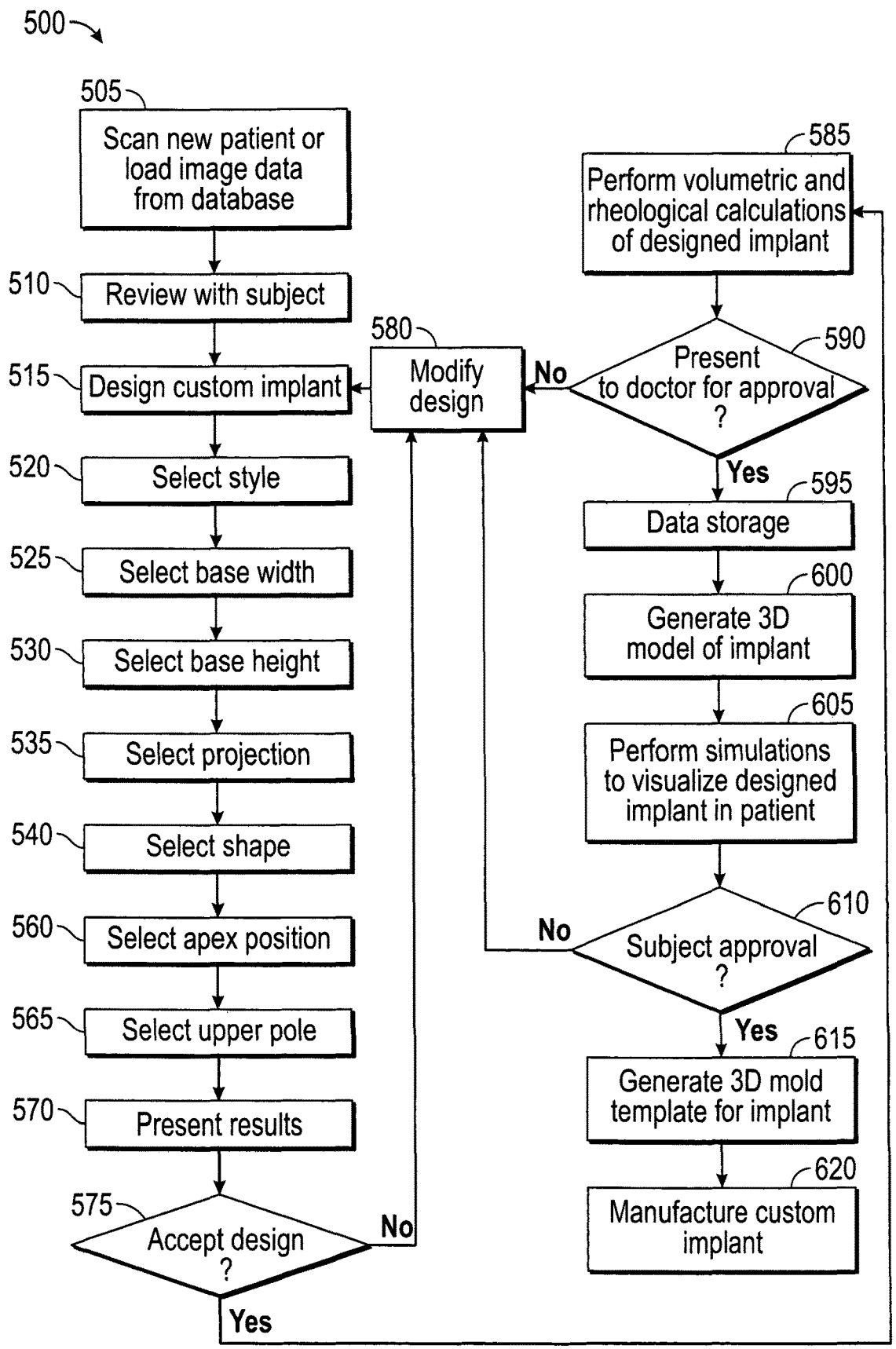
FIG. 20 is a flow chart of an exemplary method for designing a custom breast implant using the imaging system of FIG. 1.

In some embodiments, a custom implant may be designed for embedding in a patient using the imaging system 100. Although any type of implant can be designed, only the design of a custom breast implant is discussed below. FIG. 20 is a flow chart that illustrates an exemplary method 500 for designing a custom breast implant. As with the previously presented flow charts, the steps illustrated in FIG. 20 are only exemplary. In different embodiments of the current disclosure, some steps may be eliminated, added, or repeated based on the particular circumstances (e.g., needs or desired of the user or subject). A new subject is scanned using the scanner 10 or the image data associated with an existing subject is loaded into computer system 90 from the database (step 505). A digital 3D model of the subject's torso is then recreated from the image data and relevant measurements of the torso made (as discussed previously). The results of these simulations (e.g., digital 3D model displayed in the display device 92, etc.) are reviewed with the subject (step 510). The type of implant desired by the subject is then determined, e.g., based on discussions between the subject and the subject's healthcare provider.

Figure 21:
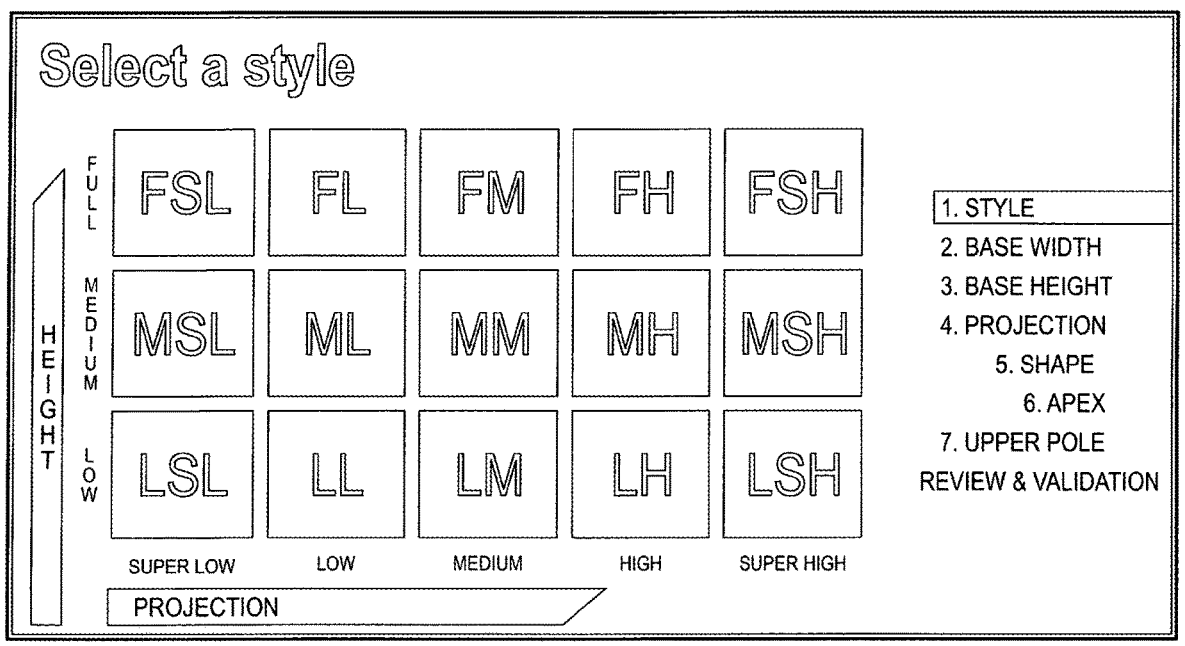
FIG. 21 illustrates an exemplary GUI of the custom breast implant design module of the imaging system of FIG. 1.

A custom implant may now be designed based on the subject's preferences and requirements (step 515). This design may be performed on the computer system 90 using a software algorithm configured for this purpose. A user may initiate the design of the custom implant by launching the algorithm in computer system 90 (e.g., by clicking on an virtual icon, pressing a keyboard key, etc.). In some embodiments, a window (or GUI) may be displayed on the display device 92 when the design algorithm is launched. The user may now be directed through several steps and prompted to enter details of the desired custom implant. In some embodiments, the user may first be prompted to select the style of the implant (step 520). FIG. 21 shows various exemplary style options the user may choose from in some embodiments of an implant design algorithm. The illustrated styles in FIG. 21 are based on combinations of height and projection of the desired implant. The user may choose a particular style of the implant (e.g., LSL—which represents an implant with a low height and a low projection) by clicking on the corresponding box (or touching on the screen in case the display device 92 is touch sensitive) representing the style in the window.

The user is then prompted to select values for different design parameters of the implant. For example, the user may first be prompted to select a value for the implant base width (step 525). Base width is the desired width of the implant at the base. The user may select the base width based on the previously made measurements from the digital 3D model of the subject's torso. In some embodiments, a range of values (e.g., a range of about 5 cm to about 16 cm, e.g., values of 5, 6, 7, 8, 9, 10, 11, 12, 13, 14, 15, or 16 cm) may be displayed on the selection screen, and the user may select a desired base width by clicking on the values displayed on the window. In some embodiments, when the user clicks on a value, a pictorial representation of an implant having the selected width (and the previously selected type) may be presented in the window. After the base width is selected, the user may then be prompted to enter another parameter, for example, the base height of the implant (see step 530). Base height is the desired height of the implant at the base. In some embodiments, the algorithm may display another window adapted to enable the user to select the base height. This window may include a range of height values (e.g., a range of about 5 cm to about 16 cm, e.g., values of 5, 6, 7, 8, 9, 10, 11, 12, 13, 14, 15, or 16 cm) that a user may select from. In some embodiments, the range of values (for base width, base height, etc.) presented in the selection window may depend upon the values selected by the user during a previous prompt (e.g., based on the style selected in step 520). The user may select a base height for the implant by clicking on the desired height value, and a pictorial representation of the implant having the previously selected base width, height, and style is presented on the window.

In a similar manner, the user may select other parameters, such as the projection (step 535), shape (540), apex position (560), and upper pole (565) for the desired implant from windows presented on the display device 92. Exemplary values of projection range from about 1 cm to about 10 cm, e.g., values of 1, 2, 3, 4, 5, 6, 7, 8, 9, or 10 cm. The projection may be less than or equal to 50% the width of the custom implant. In some embodiments, the user may be prompted to select the desired shape of the implant from different perspectives. For example, the user may be prompted to select the desired shape of the implant when viewed from the side and when viewed from the front. In some embodiments, the shape of the implant when viewed from the side may be selected as a percentage of the height of the implant using a slider scale presented on the selection window. In some embodiments, different exemplary (or available) shapes of the implant may be presented to the user, and the user may be prompted to select a desired shape from amongst the presented options. For example, different implant shapes in a front view (tear drop, oval, etc.) may be presented on a selection window, and the user may be prompted to select a shape by clicking on the icons in the window. When the desired shape of the implant is selected, a pictorial representation of the implant may be pictorially presented on the window. In some embodiments, the view point of the pictorial representation may be changed (e.g., from a side view to a front view) by clicking on icons (e.g., "select view") presented in the window. In some embodiments, the illustrated representation of the implant may be viewed in different orientations and/or rotated on the screen (e.g., by using the mouse, clicking on the arrow keys, etc.) to enable the user to design, view, and select an appropriate implant.

After the general shape is selected, in some embodiments, the user may be prompted to select the apex position of the implant (step 560). Apex position indicates the position of the nipple along the height of the implant. In some embodiments, the apex position may be selected as a percentage of the implant height (e.g., 45%, 40%, 35%, 30%, etc. of height). In some embodiments, the selected apex position may be presented in the image of the implant illustrated in the computer screen. The user may now be prompted to select the upper pole of the implant (step 565). Upper pole is an indicator of the profile shape/fullness of the upper portion of the breast, and it may be selected as a percentage of the projection. Exemplary values of upper pole positioning, expressed as a percentage of projection, range from about 50% to about 70%, e.g., values of 50%, 60%, or 70%.

In some embodiments, the user may also be prompted (or otherwise enabled) to select other parameters (e.g., viscosity of a filling material, such as a silicone filling gel (e.g., which may affect the feel of the implant with respect to simulating natural tissue), surface texture (e.g., surface characteristics of the outer implant shell, such as, e.g., roughness, kurtosis, and/or skewness, among other surface characteristics), implant volume, etc.) of the customized implant. The parameters may include any of the features or characteristics of implants, including surface texture, disclosed in U.S. Provisional Application No. 62/334,667 filed on May 11, 2016 and/or U.S. Provisional Application No. 62/410,121 filed on Oct. 19, 2016, each incorporated by reference herein in its entirety. Once all the design parameters of the implant are selected by the user, the algorithm may generate a digital 3D model of a customized implant that best fit the user's selections, and presents the results in the window (step 570). The presented results may include the configuration/shape of the designed implant along with the user-selected design parameters. In some embodiments, the orientation of the image (of the implant) illustrated in the window may be changed (rotated, zoomed, etc.) by the user. The user may now review the designed implant (step 575), accept the design (step 575=yes), or make modifications to the design (step 580). Modifications to the design can be made by repeating any of the previously described steps. For example, if the user wants to make changes to the selected style of the implant, the user may click on an icon corresponding to "style" in the GUI, to go back and change the style of the implant. In a similar manner, the user may make any desired changes to the designed implant.

After the user is satisfied with the designed implant, the algorithm may perform computations on the design (step 585). For example, in some embodiments, the algorithm may calculate volumetric and rheological parameters of the designed implant. The results (3D model, user-selected design parameters, algorithm-calculated parameters, etc.) may then be presented to a physician (e.g., plastic surgeon) for approval (step 590). If the doctor approves the design (i.e., step 590=yes), the design files may be stored in a database (step 595), and a digital 3D model of the implant may be created by computer system 90 for simulations (step 600). Simulations may now be performed by the computer system 90 to virtually embed (or implant) the designed implant in the digital 3D model of the subject's breast (obtained from step 505) to visualize the implant in the subject (step 605). In some examples, approval may not be sought or required to perform a simulation with the customized implant. The results (e.g., digital 3D model, etc.) may then be presented to the subject for approval (step 610). If the subject (and the physician) approves (step 610=yes), a computer-readable 3D model or 3D mold file of the designed implant may be created (step 610). Thus, for example, the computer-readable 3D model or mold file may be provided to a manufacturer, and the customized implant may be manufactured (step 620) based on the 3D model or mold file. In some embodiments, the implant manufacturer may use the 3D mold file to generate a tactile implant mold, e.g., via a computer numerical control (CNC) system or by 3D printing, to assist in the manufacturing process.

In some aspects of the present disclosure, the 3D model or mold file may be used to generate a custom-shaped breast implant mandrel, e.g., for manufacturing an implant shell via a dip-molding process. The customized mandrel may have a mirror image of the desired implant surface texture (e.g., desired combination of roughness, kurtosis, and skewness values) in order to produce an implant shell with the desired surface texture. Quality inspection of the customized mandrel may be performed prior to production of the implant. In some aspects, the customized mandrel may be prepared via 3D printing technology. The customized mandrel may be reusable or may be single use. In some examples, the mandrel may be single use and materials used for the mandrel may be reused, e.g., by grinding, chopping, dissolution, and/or melting. For example, the materials may be used to prepare a mandrel of a different customized design.

In some embodiments, the imaging system 100 may also be used to design accessories that are related to an implant (for e.g., garments complementary to a subject's physique before and/or after receiving an implant). For example, the system may include algorithms to generate a 3D image of a customized garment, including, but not limited to, custom bras, swim suits, and other articles of clothing. After scanning a subject and generating a 3D image (corresponding to the subject's body as-scanned or a simulation thereof), the system may allow a user to select from an available list of options/styles and/or to create a garment to fit the 3D image.

Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description. For example, while certain features have been described in connection with various embodiments, it is to be understood that any feature described in conjunction with any embodiment disclosed herein may be used with any other embodiment disclosed herein.

We claim:

1. An imaging system comprising:
a scanner comprising:
a cart coupled to a rail, wherein (a) the cart is configured to move along the rail in a first direction, and (b) the rail is configured to move with the cart in a second direction transverse to the first direction;
an imaging device including one or more cameras coupled to the cart, the imaging device being configured to rotate about an axis extending in the second direction and to capture image data of an anatomical region of a subject;
one or more light sources;
one or more sensors configured to detect a position of the cart on the rail;
a first motor configured to move the one or more cameras along the rail in the first direction, and
a second motor configured to move the cart with the one or more cameras in the second direction; and
a computer system operatively coupled to the scanner, the computer system being configured to:
control the first motor and the second motor;
rotate the one or more cameras about a second axis extending in the second direction while the one or more cameras are moving in the first direction;
receive the image data from the scanner; and
construct a three-dimensional image of the anatomical region based on the image data.

2. A method of operating a scanner including one or more light sources and one or more cameras configured to capture a three-dimensional image of a subject, the method comprising:
activating the one or more light sources by selectively activating one or more white lights and one or more yellow lights of the scanner based on a skin tone of the subject;
activating the one or more cameras, wherein the one or more cameras are coupled to a cart movably coupled to a rail;
moving the cart along the rail in a first direction; and
moving the cart along the rail in a second direction different from the first direction.

3. The imaging system of claim 1, wherein the one or more light sources include one or more white lights and one or more yellow lights.

4. The imaging system of claim 1, wherein the rail is curved in an arc.

5. The imaging system of claim 1, wherein the imaging device includes multiple cameras with different focal points.

6. The method of claim 2, further comprising rotating the one or more cameras about an axis extending in the second direction.

7. The method of claim 2, wherein activating the one or more light sources further includes adjusting an intensity of the one or more white lights and the one or more yellow lights.

8. The method of claim 2, wherein the rail is curved in an arc and extends from a first end to a second end, and wherein moving the cart along the rail includes (a) moving the cart to the first end, and (b) moving the cart from the first end to the second end.

9. The method of claim 8, wherein
moving the cart to the first end includes rotating the one or more cameras by an angle between about 5-30 degrees about the axis extending in the second direction as the cart moves towards the first end, and
moving the cart from the first end to the second end includes rotating the one or more cameras by an angle between about negative 5-30 degrees about the axis as the cart moves towards the second end.

10. The method of claim 8, wherein moving the rail with the cart includes moving the rail in the second direction after (a) moving the cart to the first end, and before (b) moving the cart from the first end to the second end.

11. The method of claim 2, wherein moving the cart and moving the rail with the cart together move the one or more cameras along a substantially rectangular path.

12. The imaging system of claim 1, wherein the computer system is configured to control the first motor and the second motor to move the one or more cameras in a substantially rectangular path.

13. The imaging system of claim 1, wherein the one or more light sources of the scanner includes one or more white lights and one or more yellow lights, and the computer system is further configured to selectively activate the one or more white lights and one or more yellow lights based on a skin tone of the subject by increasing a number of yellow lights activated as compared to the number of white lights activated for a darker skin tone, and increasing a number of white lights activated as compared to the number of yellow lights activated for a lighter skin tone.

14. The method of claim 2, wherein:
moving the cart along the rail in the first direction includes moving the one or more cameras from an original location to a first end of the scanner, and
moving the cart along the rail in the second direction includes moving the one or more cameras in the second direction for a first time period while the one or more cameras are at the first end.

15. The method of claim 14, further including:
moving the one or more cameras in a direction opposite the first direction to a second end of the scanner opposite the first end,
moving the one or more cameras in direction opposite the second direction for the first time period while the one or more cameras are at the second end, and
moving the one or more cameras in the first direction to the original location.

16. The method of claim 15, further including:
rotating the one or more cameras about a first axis by an angle between about 5-30 degrees when the one or more cameras are moving from the original location to the first end, and
rotating the one or more cameras by about negative 5-30 degrees about the first axis when the one or more cameras are moving from the original location to the second end, wherein the first axis is an axis extending along the second direction.

* * * * *